United States Patent
Tsuji et al.

(10) Patent No.: US 11,172,854 B2
(45) Date of Patent: Nov. 16, 2021

(54) SYSTEM THAT MEASURES DIFFERENT STATES OF A SUBJECT

(71) Applicant: Hitachi, Ltd., Tokyo (JP)

(72) Inventors: Satomi Tsuji, Tokyo (JP); Kazuo Yano, Tokyo (JP); Nobuo Sato, Tokyo (JP); Miki Hayakawa, Tokyo (JP); Koji Ara, Tokyo (JP); Tomoaki Akitomi, Tokyo (JP)

(73) Assignee: Happiness Planet, Ltd., Kokubunji (JP)

( * ) Notice: Subject to any disclaimer, the term of this patent is extended or adjusted under 35 U.S.C. 154(b) by 281 days.

(21) Appl. No.: 15/661,960

(22) Filed: Jul. 27, 2017

(65) Prior Publication Data
US 2017/0319125 A1    Nov. 9, 2017

Related U.S. Application Data

(63) Continuation of application No. PCT/JP2015/053026, filed on Feb. 4, 2015.

(51) Int. Cl.
*A61B 5/16* (2006.01)
*A61B 5/11* (2006.01)
*A61B 5/00* (2006.01)

(52) U.S. Cl.
CPC ............ *A61B 5/165* (2013.01); *A61B 5/0022* (2013.01); *A61B 5/11* (2013.01); *A61B 5/1123* (2013.01);
(Continued)

(58) Field of Classification Search
CPC .......... A61B 5/165; A61B 5/167; A61B 5/16; A61B 5/163; A61B 5/0022; A61B 5/0024;
(Continued)

(56) References Cited

U.S. PATENT DOCUMENTS 9,486,161 B2 * 11/2016 Ara ........................ A61B 5/11
2009/0040231 A1 * 2/2009 Sano ...................... G06T 13/40
345/474
(Continued)

FOREIGN PATENT DOCUMENTS

JP      2011-101746 A      5/2011
WO   WO 2012/169003 A1    12/2012

OTHER PUBLICATIONS

Toru Nakamura et al., "Universal Scaling Law in Human Behavioral Organization," Physical Review Letters, Sep. 28, 2007, vol. 99, Issue 13, pp. 138103-1-4 (four (4) pages).
(Continued)

*Primary Examiner* — Matthew Kremer
*Assistant Examiner* — Avery M Foley
(74) *Attorney, Agent, or Firm* — Crowell & Moring LLP

(57) ABSTRACT

An analysis system analyzes a state of a person and includes a terminal configured to be worn on the person's body. The terminal includes an acceleration sensor, a storage unit, and a processing unit. The processing unit determines whether each value contained in the time series data is in a first state in which the value is equal to or greater than the threshold or in a second state in which the value is less than the threshold. The processing unit also determines a duration which is a period of time during which the first state continues. The processing unit quantifies a brain state of the person on the basis of the duration.

5 Claims, 17 Drawing Sheets

(52) U.S. Cl.
CPC ............ *A61B 5/1126* (2013.01); *A61B 5/162* (2013.01); *A61B 5/6801* (2013.01); *A61B 5/7278* (2013.01); *A61B 5/742* (2013.01); *A61B 2562/0219* (2013.01)

(58) Field of Classification Search
CPC ....... A61B 5/0015; A61B 5/11; A61B 5/1101; A61B 5/1121; A61B 5/1123; A61B 5/1124; A61B 5/1126; A61B 5/162; A61B 5/6801; A61B 5/7278; A61B 5/7275; A61B 5/7271; A61B 5/7282; A61B 5/742; A61B 2562/0219; G16H 40/67
See application file for complete search history.

(56) References Cited

U.S. PATENT DOCUMENTS

2013/0231947 A1\* 9/2013 Shusterman ....... A61B 5/02055
 705/2
2014/0379292 A1 12/2014 Ara et al.

OTHER PUBLICATIONS

International Search Report (PCT/ISA/210) issued in PCT Application No. PCT/JP2015/053026 dated Apr. 28, 2015, with English translation (three (3) pages).
Japanese-language Written Opinion (PCT/ISA/237) issued in PCT Application No. PCT/EP2015/053026 dated Apr. 28, 2015 (four (4) pages).

\* cited by examiner

FIG. 8

| date (t0801) | time (t0802) | user_id (t0803) | ACCELERATION FREQUENCY [1/100 Hz] (t0804) | ACTIVE STATE (t0805) | COUNT (t0806) | DURATION (t0807) | CLASS (t0808) |
|---|---|---|---|---|---|---|---|
| 2011/11/1 | 10:00 | 1001 | 8 | 0 | 0 | | |
| 2011/11/1 | 10:01 | 1001 | 4 | 0 | 0 | | |
| 2011/11/1 | 10:02 | 1001 | 98 | 1 | 1 | | |
| 2011/11/1 | 10:03 | 1001 | 28 | 1 | 2 | 2 | e0 |
| 2011/11/1 | 10:04 | 1001 | 4 | 0 | 0 | | |
| 2011/11/1 | 10:05 | 1001 | 58 | 1 | 1 | | |
| 2011/11/1 | 10:06 | 1001 | 41 | 1 | 2 | | |
| 2011/11/1 | 10:07 | 1001 | 27 | 1 | 3 | | |
| 2011/11/1 | 10:08 | 1001 | 67 | 1 | 4 | | |
| 2011/11/1 | 10:09 | 1001 | 118 | 1 | 5 | 5 | e1 |
| 2011/11/1 | 10:10 | 1001 | 9 | 0 | 0 | | |
| 2011/11/1 | 10:11 | 1001 | 215 | 1 | 1 | 1 | e0 |
| 2011/11/1 | 10:12 | 1001 | 9 | 0 | 0 | | |
| 2011/11/1 | 10:13 | 1001 | 4 | 0 | 0 | | |
| 2011/11/1 | 10:14 | 1001 | 8 | 0 | 0 | | |
| 2011/11/1 | 10:15 | 1001 | 22 | 0 | 0 | | |
| 2011/11/1 | 10:16 | 1001 | 0 | 0 | 0 | | |
| 2011/11/1 | 10:17 | 1001 | 6 | 0 | 0 | | |
| 2011/11/1 | 10:18 | 1001 | 71 | 1 | 1 | 1 | e0 |
| 2011/11/1 | 10:19 | 1001 | 0 | 0 | 0 | | |
| 2011/11/1 | 10:20 | 1001 | 20 | 0 | 0 | | |
| 2011/11/1 | 10:21 | 1001 | 77 | 1 | 1 | | |
| 2011/11/1 | 10:22 | 1001 | 118 | 1 | 2 | | |
| 2011/11/1 | 10:23 | 1001 | 200 | 1 | 3 | | |
| ... | | | | | | | |
| 2011/11/1 | 10:45 | 1001 | 84 | 1 | 25 | | |
| 2011/11/1 | 10:46 | 1001 | 35 | 1 | 26 | | |
| 2011/11/1 | 10:47 | 1001 | 101 | 1 | 27 | 27 | e4 |
| 2011/11/1 | 10:48 | 1001 | 16 | 0 | 0 | | |
| 2011/11/1 | 10:49 | 1001 | 0 | 0 | 0 | | |

F I G. 9

SETTING FILE(SSSF) (TRSF)

| ITEM (SF00) | CURRENT SETTING VALUE (SF10) |
|---|---|
| ○ DEFINITION OF RANGE OF ACTIVE STATE DURATION (LD) | — |
| ・RANGE [min] (L0) | $0 < t < 5$ |
| ・RANGE [min] (L1) | $5 <= t < 10$ |
| ・RANGE [min] (L2) | $10 <= t < 15$ |
| ・RANGE [min] (L3) | $15 <= t < 20$ |
| ・RANGE [min] (L4) | $20 <= t$ |
| THRESHOLD FOR ACTIVE STATE JUDGMENT [Hz] (SF_TH) | 0.25 |
| DATA UPDATE TIME IN A DAY (SF_RE) | 2:00 am |
| CALCULATION EXPRESSION OF HAPPINESS LEVEL (SF_EQ) (e0 TO e4 ARE OCCURRENCE FREQUENCIES RESPECTIVELY CORRESPONDING TO RANGES L0 TO L4) | $H = 25 - 15.0*e1/T + 10.0*e3/T$ |

F I G. 1 3

INDEX STORAGE TABLE (SSDT_user1001)

| Date | FREQUENCY (e0) | FREQUENCY (e1) | FREQUENCY (e2) | FREQUENCY (e3) | FREQUENCY (e4) | TOTAL TIME T[min] | Happiness Value (H) |
|---|---|---|---|---|---|---|---|
| 11/1 | 34 | 4 | 5 | 8 | 1 | 579 | 26.9 |
| 11/2 | 44 | 12 | 2 | 7 | 2 | 607 | 2.0 |
| 11/3 | 22 | 4 | 8 | 14 | 0 | 738 | 34.9 |
| 11/4 | 35 | 10 | 6 | 6 | 5 | 582 | 5.3 |
| 11/5 | 9 | 2 | 4 | 10 | 3 | 606 | 36.1 |
| 11/6 | 15 | 4 | 5 | 8 | 4 | 558 | 27.0 |
| 11/7 | 21 | 3 | 7 | 7 | 1 | 613 | 27.9 |
| 11/8 | 34 | 6 | 5 | 7 | 3 | 557 | 18.8 |
| 11/9 | 22 | 5 | 10 | 7 | 4 | 576 | 22.1 |
| 11/10 | 43 | 8 | 4 | 8 | 0 | 670 | 16.1 |
| 11/11 | 26 | 5 | 9 | 9 | 2 | 642 | 25.6 |
| 11/12 | 15 | 2 | 1 | 11 | 1 | 597 | 38.0 |
| 11/13 | 30 | 7 | 12 | 9 | 3 | 750 | 20.8 |
| 11/14 | 45 | 10 | 3 | 9 | 5 | 657 | 12.2 |
| 11/15 | 58 | 13 | 8 | 8 | 0 | 825 | 7.1 |
| 11/16 | 39 | 13 | 12 | 6 | 0 | 733 | 2.1 |
| 11/17 | 0 | 0 | 0 | 0 | 0 | 0 | Null |
| 11/18 | 18 | 0 | 3 | 11 | 1 | 1351 | 33.0 |
| 11/19 | 0 | 0 | 0 | 0 | 0 | 0 | Null |
| 11/20 | 19 | 5 | 3 | 10 | 0 | 572 | 27.6 |

F I G. 1 4

USER ATTRIBUTE LIST (ASUL)

| USER NUMBER (ASUIT1) | USER NAME (ASUIT2) | TERMINAL ID (ASUIT3) | DIVISION (ASUIT4) | SECTION (ASUIT5) |
|---|---|---|---|---|
| 0 | AYUMI YAMASHITA | 1000 | "A" DIVISION | – |
| 1 | KANAE TAKAHASHI | 1001 | "A" DIVISION | "A1" SECTION |
| 2 | MASAKI SAKAI | 1002 | "A" DIVISION | "A1" SECTION |
| 3 | YOSHIYUKI ITO | 1003 | "A" DIVISION | "A2" SECTION |
| 4 | YASUNORI FUJIWARA | 1004 | "A" DIVISION | "A2" SECTION |
| 5 | HARUKA MORI | 1005 | "B" DIVISION | – |
| 6 | DAI HARADA | 1006 | "B" DIVISION | – |
| 7 | HARUO TAKEUCHI | 1007 | "C" DIVISION | "C1" SECTION |
| 8 | MISA HASEGAWA | 1008 | "C" DIVISION | "C1" SECTION |

F I G. 1 5

ACCELERATION DATA TABLE (SSDB_ACC_1002)

| | TIME (DBTM) | ACCELERATIONx (DBAX) | ACCELERATIONy (DBAY) | ACCELERATIONz (DBAZ) |
|---|---|---|---|---|
| RE01 | 20070224-13:37:45.00 | 0.10379 | 0.85863 | -0.16040 |
| RE02 | 20070224-13:37:45.02 | 0.21701 | 1.04734 | -0.65105 |
| RE03 | 20070224-13:37:47.04 | -0.00944 | 1.00959 | -0.04718 |
| RE04 | 20070224-13:37:47.06 | -0.00944 | 1.00959 | -0.04718 |

FIG. 16A

FACE-TO-FACE TABLE (SSDB_IR_1002)

|  | TIME (DBTM) | INFRARED TRANSMISSION SIDE ID1 (DBR1) | NUMBER OF RECEPTIONS 1 (DBN1) | ... | INFRARED TRANSMISSION SIDE ID10 (DBR10) | NUMBER OF RECEPTIONS 10 (DBN10) |
|---|---|---|---|---|---|---|
| RE01 | 20070219-13:37:40.00 | 1000 | 3 | ... | null | null |
| RE02 | 20070219-13:37:50.00 | null | null | ... | null | null |
| RE03 | 20070219-13:38:00.00 | null | null | ... | null | null |
| RE04 | 20070219-13:38:10.00 | 1003 | 1 | ... | null | null |
| RE05 | 20070219-13:38:20.00 | 1003 | 3 | ... | null | null |
| RE06 | 20070219-13:38:30.00 | 1003 | 6 | ... | null | null |

FIG. 16B

FACE-TO-FACE TABLE (SSDB_IR_1003)

|  | TIME (DBTM) | INFRARED TRANSMISSION SIDE ID1 (DBR1) | NUMBER OF RECEPTIONS 1 (DBN1) | ... | INFRARED TRANSMISSION SIDE ID10 (DBR10) | NUMBER OF RECEPTIONS 10 (DBN10) |
|---|---|---|---|---|---|---|
| RE01 | 20070219-13:37:40.00 | null | null | ... | null | null |
| RE02 | 20070219-13:38:10.00 | null | null | ... | null | null |
| RE03 | 20070219-13:38:20.00 | 1002 | 2 | ... | null | null |
| RE04 | 20070219-13:38:30.00 | 1002 | 4 | ... | null | null |

ACCELERATION FREQUENCY TABLE
(SSDB_ACCTP_1min)

| TIME (DBTM) | USER1001 (DBA1001) | USER1002 (DBA1002) | USER1003 (DBA1003) |
|---|---|---|---|
| 20070224-00:00:00 | 2.35 | Null | 3.65 |
| 20070224-00:01:00 | 3.10 | Null | 3.40 |
| ⋮ | ⋮ | ⋮ | ⋮ |
| 20070224-23:59:00 | 1.05 | 0.05 | 0.00 |

FIG. 18B
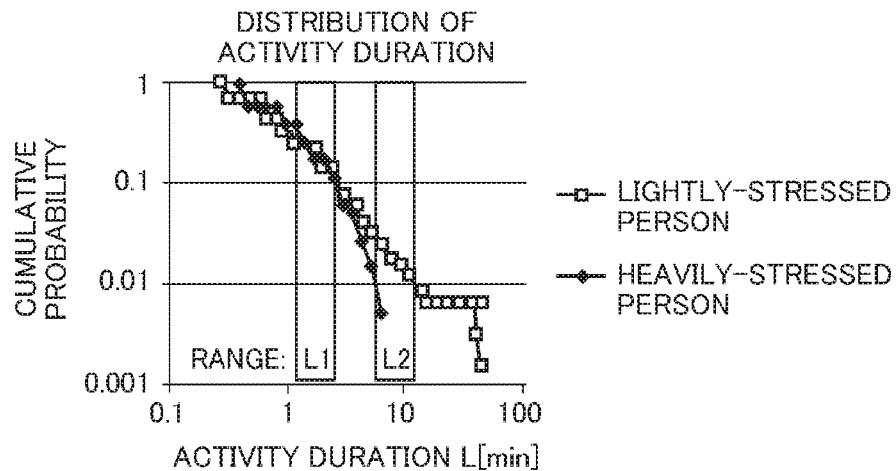
FIG. 18C
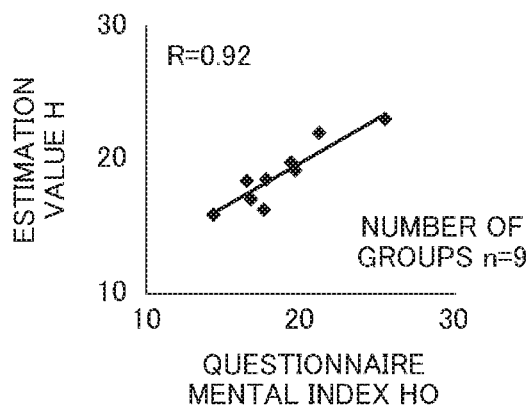
FIG. 18D
CALCULATION EXPRESSION OF
MENTAL INDEX (HAPPINESS LEVEL)
H(Happiness Value)
= a − b1*(e1/T) + b2*(e2/T)
a, b1, b2 : CONSTANTS
  (b1 AND b2 ARE POSITIVE VALUES)
T : MEASUREMENT TIME
e1 : FREQUENCY CORRESPONDING TO RANGE L1
  INTO WHICH ACTIVITY DURATION FALLS
e2 : FREQUENCY CORRESPONDING TO RANGE L2
  INTO WHICH ACTIVITY DURATION FALLS
(L1<L2)

SYSTEM THAT MEASURES DIFFERENT STATES OF A SUBJECT

TECHNICAL FIELD

Embodiments of the present invention relate to systems for measuring different states of a subject, and more concretely speaking, relate to a technology in which brain state of a person is measured by a device worn on the person's body.

BACKGROUND ART

In recent years, approaches have been widely spread in which factors that exert influences on indexes, which are regarded as the KPIs of companies (such as profits, manufacturing times, and costs). A brain state a person is associated with the productivity rate of the person, and Nonpatent Literature 1 discloses that there is a difference between the distribution profiles of productivity rates of a group of persons in healthy brain states and a group of persons in depressed brain states.

Patent Literature 1 discloses the following description in which an acceleration list is made using a sensor node equipped with a three-axis sensor, the activity judgment of a worker is made on the basis of whether the acceleration list exceeds a certain threshold or not, and an activity list for the worker is made. In this case, if this activity list includes data recorded on the second time scale, the number of seconds during which the worker is in an active state among one minute is calculated, and if the number exceeds a threshold, it is considered that the worker is active during the one minute.

CITATION LIST

Patent Literature

Patent Literature 1: WO 2012/169003

Nonpatent Literature

Nonpatent Literature: Nakamura Toru et al., "Universal Scaling Law in Human Behavioral Organization", Physical review letters, pp. 138103-1-4, 2007

SUMMARY OF INVENTION

Technical Problem

In the case where the brain state of a worker is quantified, it is preferable that motivation can be easily given to a worker. For example, it is necessary to examine with what a kind of index the brain state of a worker should be quantified in order to urge the worker to conduct himself/herself so as to become in a desirable state. To put it concretely, the quantification of the brain state, which makes it easy to grasp the current achievement status relative to a more desirable brain state and further makes it easy to give motivation to the worker so that the worker is urged to continue the abovementioned conduct, is useful. In addition, the quantification of the brain state, which makes the worker understand what kind of work has a tendency to make him/her play an improper conduct, and what kind of work has a tendency to make him/her play a proper conduct, is useful.

The embodiments of the present invention were achieved with the abovementioned problems in mind, and one of the objects of the present invention is to provide an analysis system in which the quantification of the brain state of a worker, which makes it easy to give motivation to the worker, is performed.

Solution to Problem

A representative means that is taken as an example among plural means for solving the problem according to the present invention is an analysis system for analyzing the brain state of a person and the brain state analysis system has a terminal to be worn on the person's body. The terminal includes an acceleration sensor for measuring the acceleration of motion of the body; a storage unit for storing time-series data and a threshold of the acceleration; and a processing unit for performing processing for determining whether each value contained in the time series data is in a first state in which the value is equal to or greater than the threshold or in a second state in which the value is less than the threshold, processing for determining a duration which is a period of time during which the first state continues, and processing for quantifying the brain state of the person on the basis of the duration.

Another representative means is a brain state analysis system that analyzes a brain state of a person and has a terminal to be worn on the person's body. The terminal includes: an acceleration sensor for measuring the acceleration of motion of the body; and a processing unit for calculating a first brain index that is an index showing the brain state of the person in a first time period and a second brain index that is an index showing the brain state of the person in a second time period on the basis of the time-series data of the acceleration. Here, the processing unit quantifies the influence exerted on the brain state of the person by the sensor information regarding the behavior of the person or regarding circumstances in which the person resides on the basis of the first and the second brain indexes, a first value of the sensor information in the first time period and a second value of the sensor information in the second time period.

Advantageous Effects of Invention

According to the present invention, it is possible to quantify the brain state which makes it easy to give motivation to a worker.

BRIEF DESCRIPTION OF DRAWINGS

FIG. 8 is a diagram for explaining the procedure of a brain state analysis.

FIG. 9 is an example of a diagram showing a setting file.

FIG. 13 is an example of a diagram showing an index storage table.

FIG. 14 is an example of a diagram showing a user attribute list.

FIG. 15 is an example of a diagram showing a sensing database (acceleration data).

FIG. 16(A) is an example of a diagram showing a sensing database (face-to-face data).

FIG. 16(B) is an example of a diagram showing a sensing database (face-to-face data).

FIG. 18(B) is a diagram showing the background knowledge of brain index calculation.

FIG. 18(C) is a diagram showing the background knowledge of brain index calculation.

FIG. 18(D) is a diagram showing the background knowledge of brain index calculation.

DESCRIPTION OF EMBODIMENTS

The present invention is an apparatus for measuring a brain state of a person, and is characterized in that the statistical distribution characteristic of the frequency of the duration of an active state acquired by a sensor terminal worn on the body of a person is utilized. Hereinafter, descriptions about the present invention will be made with reference to the accompanying drawings.

First Embodiment

First, a first embodiment of the present invention will be explained with reference to the accompanying drawings.

Figure 1:
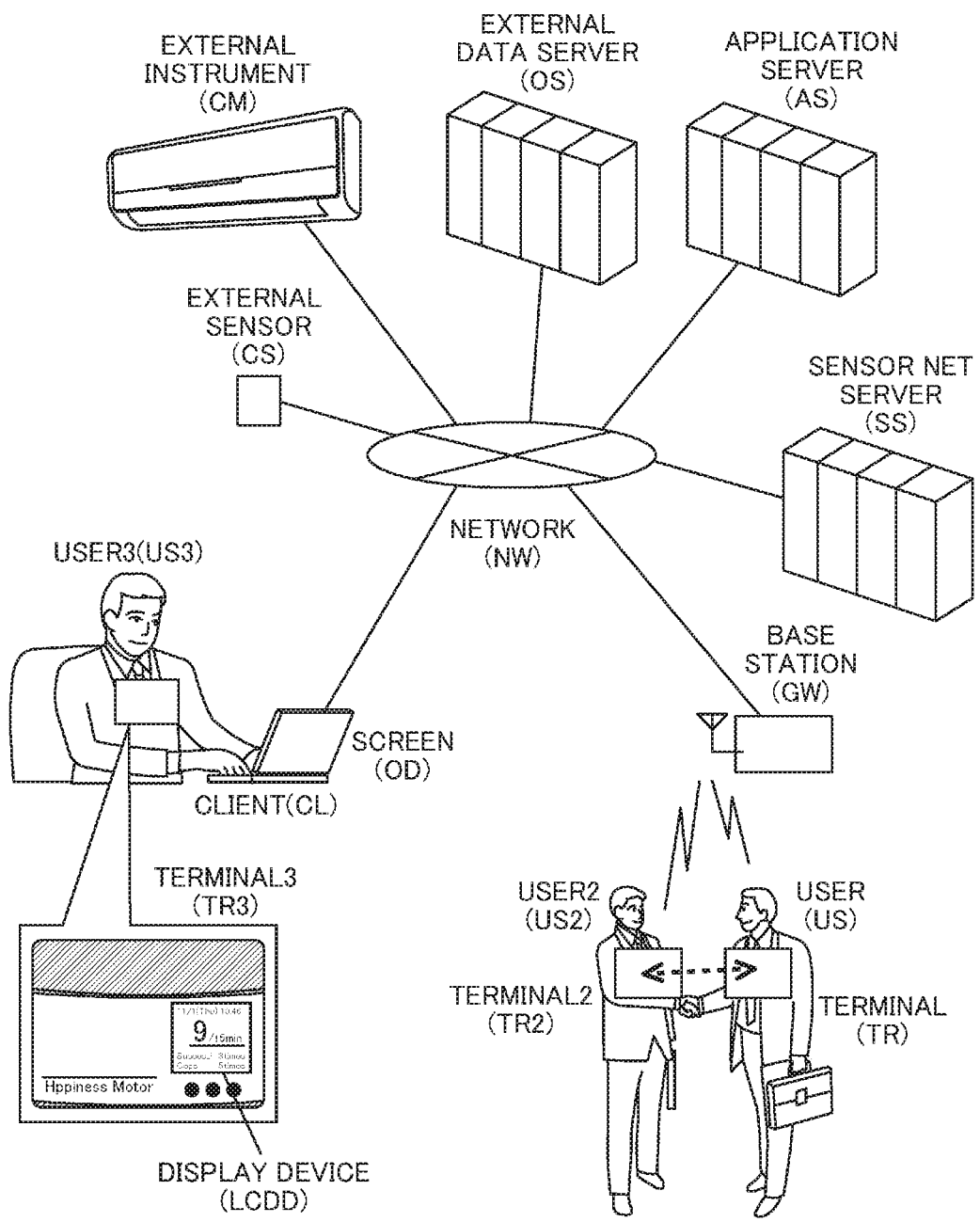
FIG. 1 is an example of a drawing showing the configuration and usage scene of a brain state measurement apparatus.

<FIG. 1: System Overview>

FIG. 1 is a diagram showing the system overview of a first embodiment. In the first embodiment, users (represented by US, US2, or US3, where, if it is unnecessary to distinguish individual users, US is used to represent a user) wear sensor terminals (represented by TR, TR2, or TR3, where, if it is unnecessary to distinguish individual terminals, TR is used to represent a terminal), and sensing data about the motion of a wearer and about a face-to-face situation (interaction) between the wearer and another wearer is acquired using a sensor (not shown) in a terminal (TR) possessed by the wearer. As for the interaction, the face-to-face situation can be detected via infrared communication between terminals (TR) possessed by two users (US) when the two users (US) meet face-to-face.

Sensing data (hereinafter, it will be assumed that the sensing data is a three-axis acceleration data, but another set of data can also be used as the sensing data) about the motion of the body of a person is processed in an in-terminal processing unit (not shown) of a terminal (TR), an index about a brain state (for example, a happiness level) is calculated by an already-stored program, and the value of the index or a numerical value about the relevant argument (for example, the frequency of the duration of an active state within a specific range) is output to a display device (LCDD) in the terminal or a display device (LCDD) connected to the terminal via wire communication or wireless communication.

On the other hand, the acquired sensing data and reference indexes (a calculated brain index and the relevant argument) are transmitted to a base station (GW) via wireless communication or wire communication, and the acquired sensing data and reference indexes are stored in a sensor net server (SS) via a network (NW). In the sensor net server (SS), an index about a brain state is calculated by a program that uses the same coefficients as the coefficients of the program used in the terminal (TR). An application server (AS) regularly acquires brain indexes about individuals or groups from the sensor net server (SS), executes a correlation analysis between the brain indexes and other conduct indexes calculated from the sensing data or indexes acquired from an external data server (OS) such as a business database, and transmits the brain indexes and graphed analysis results to a client (CL) in order for the brain indexes and the graphed analysis results to be displayed on a screen (OD).

Furthermore, in the case where the application server (AS) is connected to an external instrument (CM) that exerts an effect on the attributes of circumstances such as an air conditioner, and to an external sensor (CS) that measures those attributes, and statistical correlations between the measured values and brain indexes are analyzed by the application server (AS), it becomes possible to control the external instrument (CM) so that the brain indexes of individuals or groups under such circumstances become maximum values.

Brain states that are targets of quantification by the present invention are desirable states for an individual or a group to which the individual belongs, such as the feeling of happiness, satisfaction nourished by an employee, the feeling of fulfillment, and engagement. Conversely, it is conceivable that desirable states are indirectly measured by measuring undesirable states for the individual or the group to which the individual belongs such as the feeling of dysphoria.

Figure 2:
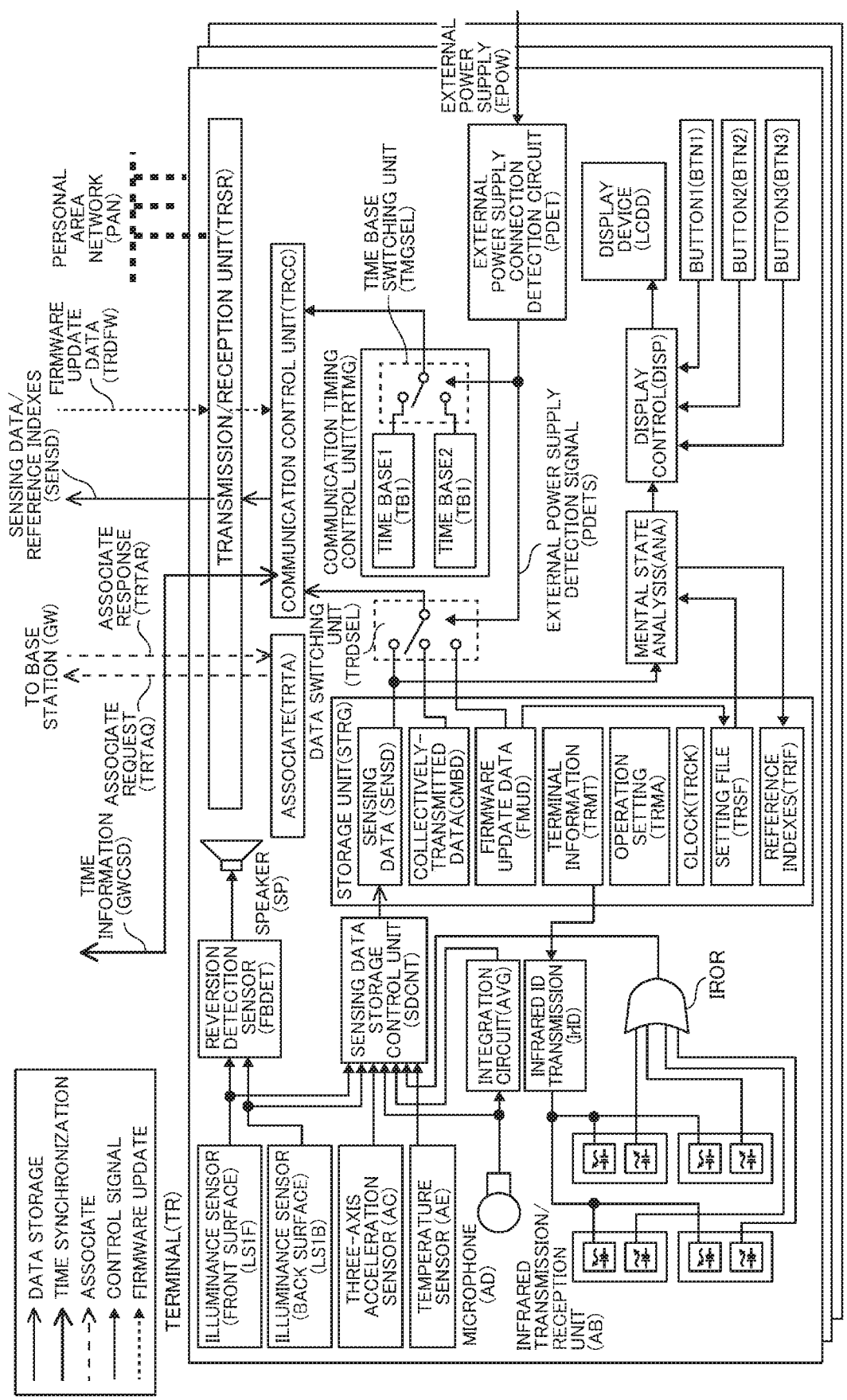
FIG. 2 is an example of a diagram showing the configuration of a terminal.
Figure 3:
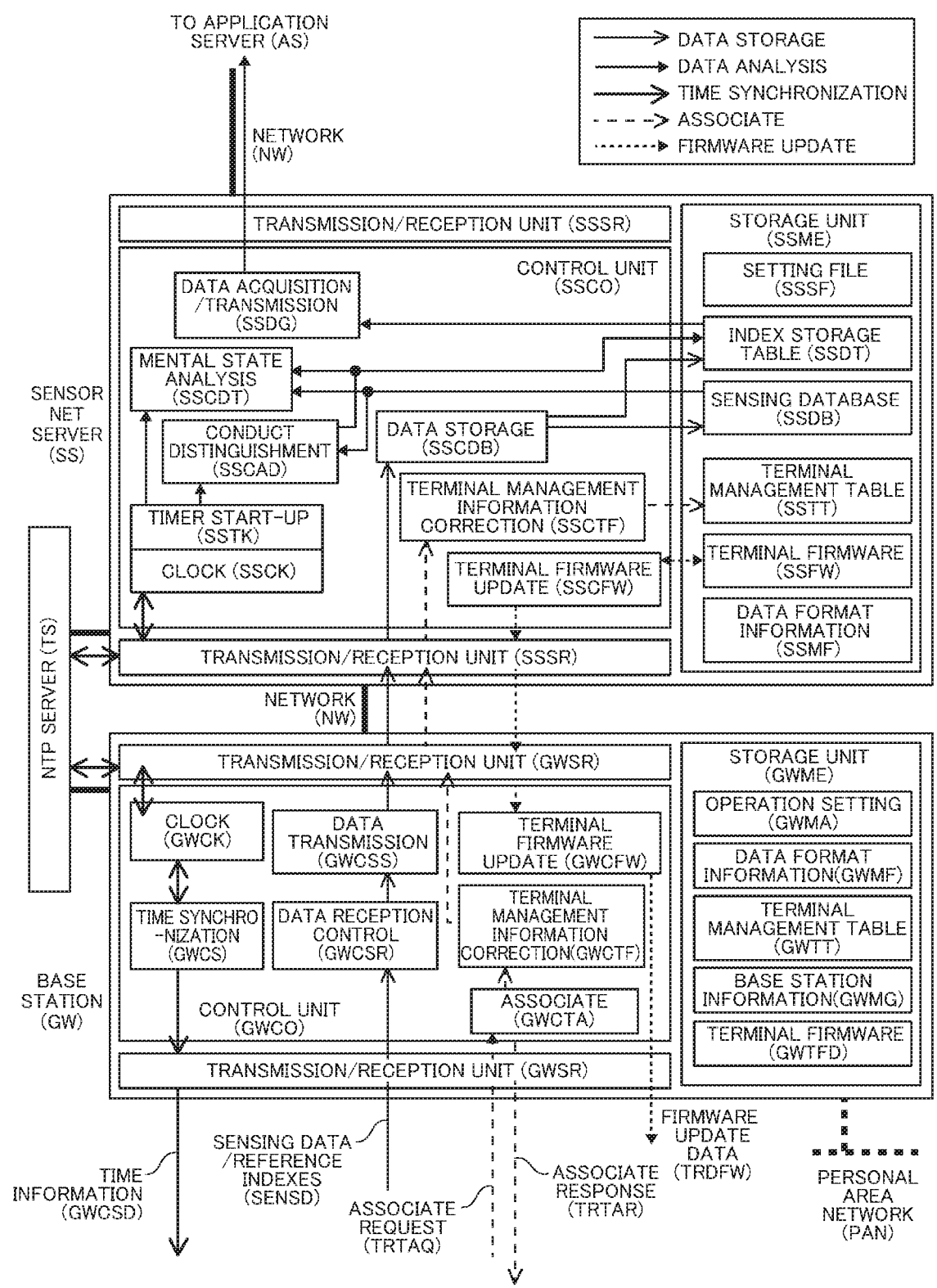
FIG. 3 is an example of a diagram showing the configurations of a sensor net server and a base station.
Figure 4:
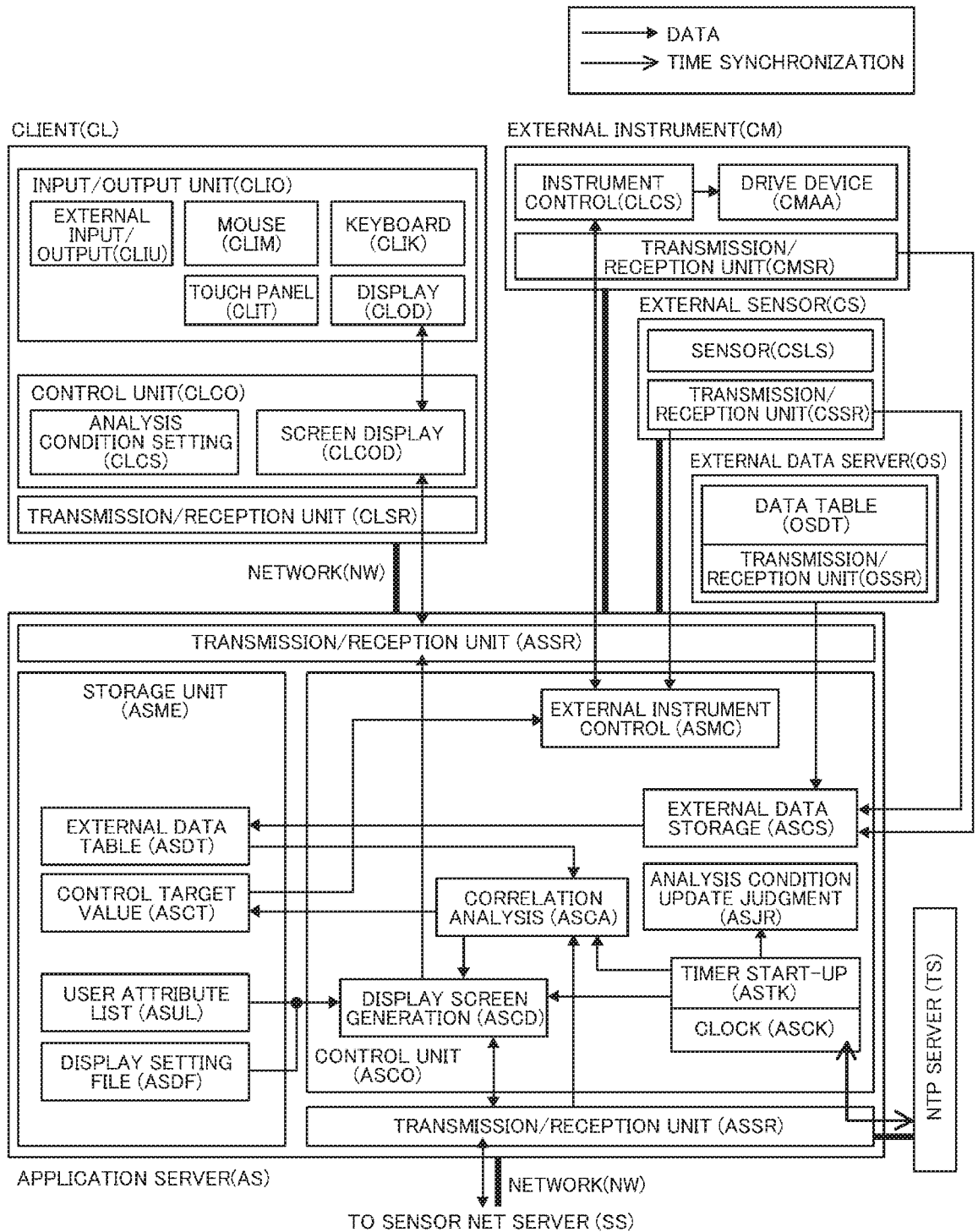
FIG. 4 is an example of a diagram showing the configurations of a client, an application server, and an instrument that is externally connected to the application server.

<FIG. 2 to FIG. 4: Block Diagrams of Entire System>

FIG. 2 to FIG. 4 are block diagrams used for explaining the entire configuration of a sensor network system of this embodiment according to the present invention. Although this embodiment is separately shown in FIG. 2 to FIG. 4 for convenience of diagrammatic representation, individual pieces of processing shown in FIG. 2 to FIG. 4 are executed in association with each other. In addition, each function depicted in FIG. 2 to FIG. 4 is realized by hardware and software in cooperation with each other. As is clear from FIG. 2 to FIG. 4, each of these components includes a control unit, a storage unit, and a transmission/reception unit. The control unit is comprised of a central processing unit (CPU, which is not shown) that is used for a processing unit of a typical computer or the like, the storage unit is comprised of a memory device such as a semiconductor storage device or a magnetic memory device, and the transmission/reception unit is comprised of network interfaces for wire communication and wireless communication. Furthermore, each of these components includes a clock and the like as needed.

Six kinds of arrows whose patterns are different from each other in FIG. 2 to FIG. 4 represent time synchronization, acquired sensing data storage, a sensing data analysis, firmware update, and the flow of data or signals for control signals respectively.

<FIG. 2: Entire System 1 (TR)>

FIG. 2 shows the configuration of a terminal (TR) that is an embodiment of a sensor node. In this case, although the terminal (TR) is in the shape of a nameplate, and it is assumed that the terminal (TR) is dangled from a person's neck, this is an example, and the terminal (TR) may be in another shape. Usually there are plural terminals (TR) in this series of system, and the plural terminals are worn by plural persons respectively. A terminal (TR) mounts plural infrared transmission/reception unit (AB) for detecting the face-to-face situation between persons, various sensors, that is to say, a three-axis acceleration sensor (AC) for detecting the motion of the wearer, a microphone (AD) for detecting the speech of the wearer and the sounds of circumstances, illuminance sensors (LS1F, LS1B) used for detecting the front surface and back surface of the terminal, and a temperature sensor (AE). The above mounted sensors are taken as examples, and another kind of sensor may be used for detecting the face-to-face situation and motion of the wearer.

This embodiment mounts four sets of infrared transmission/reception units. Infrared transmission/reception units (AB) regularly continue to transmit terminal information (TRMT) that is identification information unique to the terminal (TR) in the front direction. If a person wearing another terminal (TR) positions himself/herself approximately in front of the relevant terminal (TR) (for example, in front of or obliquely or in front of the relevant terminal (TR)), because the relevant terminal (TR) and the another terminal (TR) communicate their terminal information to each other, each terminal (TR) can record who meets whom face-to-face. In addition, the terminal (TR) transmits and receives positional information to and from the position detector (not shown) installed in external circumstances, hence the terminal (TR) can detect which user (US) stays in that area.

Generally speaking, each infrared transmission/reception unit includes a combination of an infrared light-emitting diode and an infrared light-emitting phototransistor for infrared transmission. An infrared ID transmission unit (IrID) generates the terminal information (TRMT) as its own ID, and transfers the terminal information to infrared light-emitting diodes of the infrared transmission/reception modules. In this embodiment, because the same data is transmitted to the plural infrared transmission/reception modules, all the infrared light-emitting diodes turn on at the same time. It goes without saying that different data can be separately output to the respective infrared transmission/reception modules in independent timings respectively.

Furthermore, data received by the infrared phototransistors of an infrared transmission/reception unit (AB) is logically added by a logical addition circuit (IROR). In other words, if at least one infrared phototransistor of the infrared reception unit optically receives ID information, the ID is recognized by the terminal. It goes without saying that the terminal can include plural ID reception circuits independent of each other. In this case, because it becomes possible to grasp the transmission/reception situations of the respective infrared transmission/reception modules, additional information, such as information about in which direction another terminal meeting the relevant terminal face-to-face is standing, can be acquired.

Sensing data (SENSD) detected by the sensors is stored in a storage unit (STRG) by a sensing data storage control unit (SDCNT). The sensing data (SENSD) is converted into transmission packets by a transmission/reception control unit (TRCC), and the transmission packets are transmitted to the base station (GW) by a transmission/reception unit (TRSR).

In the above case, it is a transmission/reception timing control unit (TRTMG) that decides a timing in which the sensing data (SENSD) is brought out from the storage unit (STRG) and transmitted via the wireless or wire communication. The transmission/reception timing control unit (TRTMG) includes plural time bases (TB1 and TB2) for deciding plural timings.

Data stored in the storage unit includes collectively-transmitted data (CMBD) that was accumulated in the past and firmware update data (FMUD) for updating firmware which includes an operation program of the terminal, in addition to sensing data (SENSD) detected just now by sensors.

The terminal (TR) of this embodiment detects that it is connected to an external power supply (EPOW) by an external power supply connection detection circuit (PDET), and generates an external power supply detection signal (PDETS). A time base switching unit (TMGSEL) that switches a transmission timing generated by the timing control unit (TRTMG), and a data switching unit (TRDSEL) that switches data that is transmitted or received wirelessly are configurations unique to this terminal (TR) FIG. 2 shows, as an example, a configuration in which the time base switching unit (TMGSEL) switches the transmission timing by selecting between the time base 1 (TB1) and the time base 2 (TB2) in accordance with the external power supply detection signal (PDETS). In addition, FIG. 2 shows a configuration in which the data switching unit (TRDSEL) switches data to be transmitted by selecting among the sensing data (SENSD) acquired by sensors, the collectively-transmitted data (CMBD) that was accumulated in the past, and the firmware update data (FMUD) in accordance with the external power supply detection signal (PDETS).

The illuminance sensors (LS1F, LS1B) are mounted on the front surface and back surface of the terminal (TR) respectively. Data items acquired by the illuminance sensors (LS1F, LS1B) are stored in the storage unit (STRG) by the sensing data storage control unit (SDCNT), and at the same time, the data items are compared with each other by a reversion detection unit (FBDET). If the nameplate is correctly mounted, the illuminance sensor (LS1F) mounted on the front surface receives incoming light, and the illuminance sensor (LS1B) mounted on the back surface does not receive the incoming light because the illuminance sensor (LS1B) is sandwiched between the body of the terminal and the wearer. In this case, illuminance detected by the illuminance sensor (LS1F) is larger than that detected by the illuminance sensor (LS1B). On the other hand, when the terminal (TR) is reversed, the illuminance sensor (LS1B) receives the incoming light, and because the illuminance sensor (LS1F) faces the wearer, illuminance detected by the illuminance sensor (LS1B) is larger than that detected by the illuminance sensor (LS1F).

In this case, through the reversion detection unit's (FBDET) comparing the illuminance detected by the illuminance sensor (LS1F) and that detected by the illuminance sensor (LS1B), it can be detected that the nameplate node is reversed and is not correctly mounted. When the reversion detection unit (FBDET) detects the reversion of the nameplate node, an alarm sound is issued from a speaker (SP) and the wearer is informed of the reversion of the nameplate node.

The microphone (AD) acquires sound information. Judging from the sound information, the surrounding circumstances can be judged as "noisy" or "calm". Furthermore, by acquiring and analyzing the speeches of persons, conduct indexes about face-to-face communication, such as an index whether communication is active or non-active, an index whether a conversation is exchanged on an equal basis or on a unilateral basis, and an index whether a person is angry or laughing, can be generated. In addition, a face-to-face situation that cannot be detected by the infrared transmission/reception unit (AB) owing to positions in which persons stand can also be corrected using the sound information and acceleration information.

With the use of the sound acquired by the microphone (AD), both sound waveform and signal are acquired, where the signal is acquired by integrating the sound using integration circuit (AVG). This signal acquired by the integration is considered to represent the energy of the acquired sound.

The three-axis acceleration sensor (AC) detects the acceleration of a node, that is to say, the motion of the node. Therefore, the intensity of the motion of a person who wears a terminal (TR) and the behaviors of the person, such as walking, can be analyzed using the acceleration data. Furthermore, by comparing the values of accelerations detected by plural terminals in the same time period, the degree of activity of communication, mutual rhythms, mutual correlations, and the like among persons who wear those terminals can be analyzed.

In the terminal (TR) of this embodiment, data acquired by the three-axis acceleration sensor (AC) is stored in the storage unit (STRG) by the sensing data storage control unit (SDCNT).

Brain state analysis (ANA) reads a setting file (TRSF) that has already been stored in the storage unit (STRG), calculates the frequencies of the duration of an active state within a specific range using the program, and calculates the linear sum of the frequencies using coefficients that are similarly specified, hence a brain index is calculated using the calculated linear sum. Subsequently, values (brain indexes and the frequencies of duration) in the reference indexes (TRIF) stored in the storage unit (STRG) are updated in association with the update time, and the displayed values are also updated and displayed on the display device (LCDD) again through display control (DISP). It is conceivable that the displayed content is switched by pushing any of buttons (BTN1 to BTN3).

Through the transmission/reception of infrared lights between nodes executed by the infrared transmission/reception unit (AB), it is detected whether the terminal (TR) met another terminal (TR) face-to-face or not, that is to say, whether the person wearing the terminal (TR) met a person wearing another terminal (TR) or not. Therefore, it is desirable for the terminal (TR) to be worn on the front region of the person. As mentioned above, the terminal (TR) further includes sensors such as the three-axis acceleration sensor (AC). The sensing process executed in the terminal (TR) corresponds to sensing (TRSS1) shown in FIG. 5.

Usually there are plural terminals, and in the case where the terminals and base stations are connected via wireless connections, each of the terminals is connected to a nearby base station (GW), with the result that a combination of the terminal and the nearby base station forms a personal area network (PAN).

The temperature sensor (AE) of the terminal (TR) acquires the temperature in a site where the terminal (TR) is located, and the illuminance sensor (LS1F) acquires the illuminance in the front direction of the terminal (TR) and the like. Therefore, the surrounding circumstances of the terminal can be recorded. For example, the fact that the terminal (TR) moves from one place to another can be known on the basis of the temperature and illuminance.

As input/output devices corresponding to the person wearing the terminal (TR), the button 1 to button 3 (BTN1 to BTN3), the display device (LCDD), the speaker (SP), and the like are provided.

Concretely speaking, the storage unit (STRG) is comprised of nonvolatile memory devices such as a hard disk and a flash memory, and records terminal information (TRMT) that includes an identification number unique to the terminal (TR), a sensing interval, and operation setting (TRMA) including output contents to the display and the like. As for another function, the storage unit (STRG) can temporarily record data, so that it is used for recording sensing data.

A clock (TRCK) holds time information (GWCSD), and updates the time information (GWCSD) at certain intervals. The clock (TRCK) corrects time using time information (GWCDS) regularly transmitted by a base station (GW) in order to prevent the time information (GWCDS) from differing from time information held by other terminals (TR).

The sensing data storage control unit (SDCNT) controls sensing intervals for the respective sensors in accordance with the operation setting (TRMA) recorded in the storage unit (STRG), and manages acquired data.

Time synchronization is executed by correcting the clock (TRCK) using time information acquired from the base station (GW). The time synchronization can be executed just after an after-mentioned associate, or can be executed in accordance with a time synchronization command transmitted by the base station (GW).

The transmission/reception control unit (TRCC) controls transmission intervals, and converts the format of data into a data format well-adapted to wireless transmission/reception when the data is transmitted or received. The transmission/reception control unit (TRCC) may be equipped with a wire communication function if needed instead of the wireless communication function. The transmission/reception control unit (TRCC) executes congestion control in some cases in order to prevent the transmission timing of its own from overlapping the transmission timings of other terminals (TR).

An associate (TRTA) transmits an associate request (TRTAQ) and receives an associate response (TRTAR) for establishing a personal area network (PAN) in cooperation with a base station (GW), and decides a base station (GW) to which data should be transmitted. The associate (TRTA) is executed when the power supply of the terminal (TR) is turned on or when the transmission/reception between the terminal (TR) and the current base station (GW) is disconnected owing to the displacement of the terminal (TR). In the case where a wire connection is used, the associate (TRTA) is executed when it is detected that the terminal (TR) is connected to a base station (GW) via a wire connection. As a result of the associate (TRTA), the terminal (TR) is associated with one base station (GW) located within a range covered by wireless signals issued from the terminal (TR).

The transmission/reception unit (TRSR) is equipped with an antenna, and transmits and receives wireless signals. The transmission/reception unit (TRSR) is capable of performing transmission and reception using a connector for wire communication if needed. Sensing data and reference indexes (SEND) transmitted or received by the transmission/reception unit (TRSR) are transferred via a personal area network (PAN) established between the terminal (TR) and the base station (GW).

<FIG. 3: Entire System 2 (GW and SS)>

FIG. 3 shows the configurations of an embodiment of a sensor net server (SS) and a base station (GW).

<Base Station (GW)>

A base station (GW) plays a role for mediating between a terminal (TR) and a sensor net server (SS). If wireless communication is used, there is a case where plural base stations (GW) are used for connection with the terminal (TR) taking the coverage of the wireless communication into consideration so that a range including a living room, a working place, and the like is covered. If wire communication is used, the upper limit of the number of terminals (TR) to be managed is set in accordance with the processing capacity of a base station (GW).

A base station includes a transmission/reception unit (GWSR), a storage unit (GWME), and a control unit (GWCO).

The transmission/reception unit (GWSR) receives data from the terminal (TR) via wire or wireless communication, and transmits data to a sensor net server (SS) via wire or wireless communication. If the wireless communication is used for the transmission/reception, the transmission/reception unit (GWSR) includes an antenna for receiving the wireless communication. In addition, in order to prevent data from being lost in the transmission/reception of sensing data, the transmission/reception unit (GWSR) executes, as needed, congestion control, that is to say, communication timing control. Furthermore, the transmission/reception unit (GWSR) distinguishes the types of received data. To put it concretely, the transmission/reception unit (GWSR) distinguishes whether the received data is typical sensing data, data for associates, responses for time synchronization, or others using the header parts of the respective data, and transfers the respective data to appropriate functions.

The storage unit (GWME) is comprised of external recording devices (not shown) such as a hard disk, a memory, and an SD card. The storage unit (GWME) stores operation setting (GWMA), data format information (GWMF), a terminal management table (GWTT), base station information (GWMG), and terminal firmware (GWTFD). The operation setting (GWMA) includes the operation method of the base station (GW). The data format information (GWMF) includes information showing data formats for communication and information necessary for tagging sensing data. The terminal management table (GWTT) includes terminal information (TRMT) about terminals (TR) that are currently ruled associates, and local IDs that are delivered for managing those terminals (TR). In the case where, because the base station is connected to the ruled terminals (TR) via wire communication, it is unnecessary to always grasp the situations of the ruled terminals (TR), the terminal management table (GWTT) can be spared. The base station information (GWMG) includes the address of the base station (GW) itself, and the like. The terminal firmware (GWTFD) memorizes programs for activating terminals, and when the terminal firmware (GWTED) receives a command and new terminal firmware from the sensor net server (SS), the terminal firmware (GWTED) transmits firmware update data (TRDFW) to the relevant terminal (TR) via the personal area network (PAN) (GWCFW). The storage unit (GWME) can further store a program executed by a CPU (not shown) of the control unit (GWCO).

The control unit (GWCO) includes the CPU (not shown). The CPU executes the program stored in the storage unit (GWME), hence timings in which sensing data is received from terminals (TR), processing of sensing data, transmission/reception timings to and from terminals (TR) and the sensor net server (SS), and the timing of time synchronization are managed. To put it concretely, pieces of processing such as data reception control (GWCSR), data transmission (GWCSS), associate (GWCTA), terminal management information correction (GWCTF), terminal firmware update (GWCFW), and time synchronization (GWCS) are executed.

A clock (GWCK) holds time information. The information is updated at certain intervals. To put it concretely, the time information of the clock (GWCK) is corrected by time information acquired at constant intervals from an NTP (Network Time Protocol) server (TS).

The time synchronization (GWCS) transmits time information to the ruled terminals (TR) at constant intervals or at the time when a terminal (TR) is connected to the base station (GW). With this, times of the plural terminals (TR) and the time of the clock (GWCK) of the base station (GW) are synchronized with each other.

In response to an associate request (TRTAQ) transmitted from a terminal (TR), the associate (GWCTA) issues an associate response (TRTAR) that transmits an allocated local ID to the terminal (TR). The associate relation is established, the associate (GWTA) executes the terminal management information correction (GWCTF) in which the terminal management table (GWTT) is corrected.

The data reception control (GWCSR) receives a packet of sensing data (SENSD) transmitted from a terminal (TR). The data reception control (GWCSR) reads the header of the packet of sensing data, distinguishes the type of data, and executes congestion control lest data should arrive at the same time from many terminals (TR).

The data transmission (GWCSS) attaches the ID of a base station through which sensing data passes and the time at which the sensing data passes through the base station to the sensing data, and transmits the sensing data to the sensor net server (SS).

<Sensor Net Server>

The sensor net server (SS) includes a transmission/reception unit (SSSR), a storage unit (SSME), and a control unit (SSCO).

The sensor net server (SS) manages data getting together from all the terminals (TR). To put it concretely, the sensor net server (SS) stores sensing data transmitted from the base station (GW) in a sensing database (SSDB), and stores reference indexes transmitted from the base station (GW) in an index storage table (SSDT) (SSCDB). In addition, the sensor net server (SS) searches for data in the index storage table (SSDT) on the basis of a request from the application server (AS), and transmits the retrieved data to the application server (AS) (SSDG).

Furthermore, the sensor net server (SS) manages information about the base station (GW) and terminals (TR) ruled by the base station (GW) as needed. In addition, the sensor net server (SS) plays a role as a source from which a control command for updating the firmware of the terminals (TR). Because it is desirable that a brain index calculation program and a part of coefficients for index calculation, which are stored in a setting file (SSSF), should be synchronized with the terminals (TR), setting files (TRSF) in the terminals (TR) are updated via the route of terminal firmware update (SSCFW) when the setting file (SSSF) is corrected.

The transmission/reception unit (SSSR) transmits data to and receives data from the base station (GW), the application server (AS), personal clients (CP), or clients (CL).

The storage unit (SSME) includes data storage devices such as a hard disk, and stores at least the sensing database (SSDB), the index storage table (SSDT), data format information (SSMF), a terminal management table (SSTT), and terminal firmware (SSFW). Furthermore, the storage unit (SSME) stores a program executed by a CPU (not shown) of the control unit (SSCO).

Figures 17, 18A:
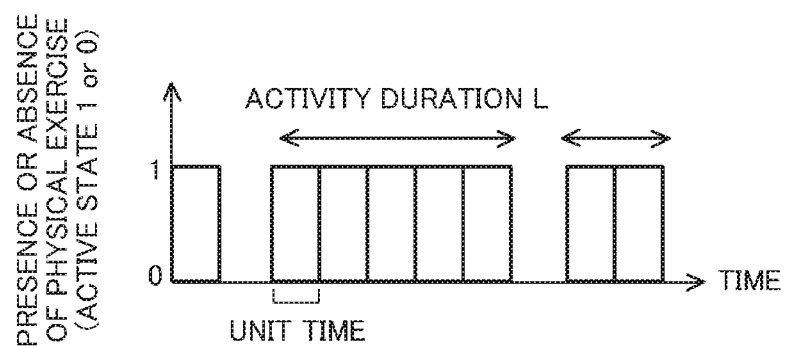
FIG. 17 is an example of a diagram showing an acceleration frequency table.
FIG. 18(A) is a diagram showing the background knowledge of brain index calculation.

The sensing database (SSDB) is a database that records sensing data that each terminal (TR) acquires, information about each terminal (TR), information about a base station (GW) through which sensing data transmitted by each terminal (TR) passes, and the like. Columns are created for respective data items such as acceleration, temperature, and these data items are managed. Alternatively, it is conceivable that tables are created for respective data items. In either case, every data item is managed in association with terminal information (TRMT) which is an ID of a terminal (TR) at which the data is acquired and information about a time at which the data is sensed. An example of an acceleration data table held by the sensing database (SSDB) is shown in FIG. 15 (SSDB_ACC_1002), examples of infrared data tables for two persons are shown in FIG. 16 (SSDB_IR_1002) and (SSDB_IR_1003), and an example of a table including acceleration frequencies (or conduct rhythms) calculated from the acceleration data in one-minute periods is shown in FIG. 17 (SSDB_ACCTP_1 min).

The data format information (SSMF) records information about data formats for communication; a method using which sensing data, which is tagged at a base station (GW), is sorted and recorded in the database; and a method which shows how to deal with data requests; and the like. After data reception or before data transmission, this data format information (SSMF) is referred to, and the format of data is converted and the data is sorted.

The terminal management table (SSTT) is a table that records which terminal (TR) is currently ruled by which base station (GW). When a terminal (TR) is newly ruled by a base station (GW), the terminal management table (SSTT) is updated. However, if a base station (GW) and a terminal (TR) are connected to each other via wire communication, it is unnecessary for the terminal management table (SSTT) to always watch terminal management information.

The terminal firmware (SSFW) holds a program for activating terminals, and when the terminal firmware update (SSCFW) is executed, the terminal firmware (SSFW) is updated, and this updated firmware is transmitted to base stations (GW) via the network (NW). Further this updated firmware is transmitted to terminals (TR) via personal area networks (PAN), so that firmware in each terminal (TR) is updated (FMUD).

The control unit (SSCO) including the CPU (not shown) controls the transmission/reception of sensing data, and recording data in and retrieving data from the database. To put it concretely, through the CPU's executing programs stored in the storage unit (SSME), pieces of processing about the data storage (SSCDB), terminal management information correction (SSCTF), terminal firmware update (SSCFW), brain state analysis (SSCDT), conduct distinguishment (SSCAD), and the like are executed.

The data storage (SSCDB) is processing in which sensing data transmitted from a base station is received and stored in the sensing database (SSDB). Additional information, such as time information, the relevant terminal ID, a time at which the sensing data passes through the base station, is attached to the sensing data, and the sensing data is stored in the database as one record.

A clock (SSCK) holds a standard time through regularly communicating with an external NTP server (TS). When the clock (SSCK) shows a predefined time, or satisfies a specific condition, timer start-up (SSTK) is executed on sensing data processing (SSCDT).

The brain state analysis (SSCDT) acquires sensing data stored in the sensing database (SSDB) or reference indexes (frequencies for respective active state durations) that are transmitted from terminals (TR) and stored in the index storage table, calculates brain indexes in predefined time periods using a program and coefficients stored in the setting file (SSSF), and stores the results in the index storage table (SSDT).

The conduct distinguishment (SSCAD) acquires sensing data acquired by terminals (TR) from the sensing database (SSDB), distinguishes conducts such as walking, desk work, meeting, and the like using a program (not shown) in the storage unit (SSME), and stores the respective data in the index storage table (SSDT) in association with time information.

On receiving a command to correct terminal management information from a base station (GW), the terminal management information correction (SSCTF) corrects the terminal management table (SSTT). This correction is executed for always grasping the list of terminals (TR) ruled by each base station (GW).

When it becomes necessary to update the firmware of terminals (TR) manually or automatically, the terminal firmware update (SSCFW) updates terminal firmware stored in the storage unit (SSME), and further issues a command to each base station (GW) so as to make each base station (GW) update the firmware of terminals ruled by each base station (GW). In this case, the terminal firmware update (SSCFW) continues receiving responses informing that the firmware update has been finished from the respective terminals (TR) until the firmware updates of all the terminals (TR) are finished.

<FIG. 4: Entire System 3 (CL and AS)>

FIG. 4 shows the configuration of an embodiment comprised of a client (CL), an application server (AS), and additionally an instrument that is externally connected and the like.

<About Client (CL)>

The client (CL) plays a role as a contact point to a user (US), and data is transmitted or received through the client. The client (CL) includes an input/output unit (CLIO), a transmission/reception unit (CLSR), a storage unit (not shown), and a control unit (CLCO).

The input/output unit (CLIO) is a component that plays a role as an interface with a user (US). The input/output unit (CLIO) includes a display (CLOD), a touch panel (CLIT), a keyboard (CLIK), a mouse (CLIM), and the like. It is also possible to connect other input/output devices to an external input/output (CLIU).

The display (CLOD) is an image display device such as a CRT (Cathode-Ray Tube) or a liquid crystal display. It is conceivable that the display (CLOD) includes a printer and the like. In the case where the touch panel (CLIT) is used to support input work made by a user, it is also possible to pretend that the input work and output work are executed on the same screen by disposing the touch panel (CLIT) so as to overlap the screen (OD) of the display (CLOD).

The transmission/reception unit (CLSR) exchanges data and commands with the application server (AS) and other devices connected to the network. To put it concretely, the transmission/reception unit (CLSR) transmits a request about a screen to be displayed to the application server (AS), and receives an image corresponding to the request.

The storage unit (not shown) is comprised of external recording devices such as a hard disk, a memory, and an SD card. It is also possible to make the storage unit (not shown) store display histories, login IDs of users (US), and the like.

The control unit (CLCO) includes a CPU (not shown), and executes pieces of processing such as screen control (CLCOD) for controlling screens to be displayed on the display (CLOD) and analysis condition setting (CLCS) used for a user (US) to inform the application server (AS) of the change of an analysis condition.

<Application Server (AS)>

The application server (AS) executes: correlation analysis (ASCA) between a brain index and other indexes such as conduct indexes, achievement indexes, and the like; optimal control (ASMC) of an external instrument; screen generation (ASCD) for proposing a brain index, the result of the correlation analysis, the state of the external instrument, and the like to the client (CL).

The application server (AS) includes a transmission/reception unit (ASSR), a storage unit (ASME), and a control unit (ASCO).

The transmission/reception unit (ASSR) exchanges data with the sensor net server (SS), the NTP server (TS), the client (CL), the external instrument (CM), the external sensor (CS), the external data server (OS) and the like via the network (NW), and executes communication control for this purpose.

The storage unit (ASME) is comprised of external recording devices such as a hard disk, a memory, and an SD card. The storage unit (ASME) stores created content information, a program used for creating contents, and other data relating to the creation of contents. To put it concretely, the storage unit (ASME) stores a user attribute list (ASUL), a display setting file (ASDF), an external data table (ASDT), and a control target value (ASCT).

The user attribute list (ASUL) is a reference table in which the ID of each terminal is listed in association with the name, user ID, division, mail address, attributes, and the like of a user (US) wearing the terminal. When an ID obtained from a conversational partner at a face-to face meeting is associated with the name of the partner, when brain indexes are aggregated for respective divisions, or when display contents are changed in accordance with IDs using which login to websites are executed, the user attribute list (ASUL) is referred to. FIG. 14 shows a concrete example of the user attribute list (ASUL).

The control unit (ASCO) includes a CPU (not shown), and executes pieces of processing such as a data analysis and screen generation. Furthermore, the application server (AS) includes a clock (ASCK), and the application server (AS) maintains the correct time of the clock (ASCK) by communicating with the external NTP server (TS). The application server (AS) executes timer start-up (ASTK) on each program stored in the control unit (ASCO) at a predefined time, and executes the program. Alternatively, it is conceivable that each program is activated manually, or when the application server (AS) receives directions from a client (CL), or each program is activated using, as a trigger, the fact that an index transmitted from the sensor net server (SS) has a specific pattern.

The display screen generation (ASCD) acquires necessary data after sending a request to the sensor net server (SS), and draws a screen with reference to the user attribute list (ASUL), the display setting file (ASDF), and additionally with reference to the result of the correlation analysis (ASCA) as needed, and transmits the drawn screen to the client (CL).

The correlation analysis (ASCA) executes a statistical analysis using brain indexes, data in the sensor net server (SS) on which the conduct distinguishment has already been executed, data acquired from the external data table (ASDT) such as business data and financial data, and extracts an index statistically associated with an index expected to be maximized. A control variable in external instrument control (ASMC) and its target value are defined on the basis of this statistical result, and these are recorded in the control target value (ASCT). In addition, if brain indexes are acquired through a questionnaire, it is conceivable that an estimation expression that calculates a brain index using a correlation analysis between conduct indexes and the brain indexes acquired through the questionnaire is updated.

Furthermore, the correlation analysis (ASCA) executes an analysis in which an influence exerted on a brain index by other indexes is quantified. To put it concretely, by executing the correlation analysis between a brain index in a first time period and in a second time period and other sensor information in the first time period and in the second time period, an influence exerted on the brain index by the sensor information can be quantified.

Analysis condition update judgment (ASJR) checks whether there is any change in the estimation expression of a brain index, coefficients of the estimation expression, or the types of arguments to be used, and if any change is necessary, the analysis condition update judgment (ASJR) transmits an update request to the sensor net server (SS), updates the setting file (SSSF), and further activates the terminal firmware update (SSCFW) to update setting files (TRSF) in terminals (TR).

External data storage (ASCS) is a process in which data is acquired from the operation log of an external instrument (CM) connected to the application server (AS), the log of the external sensor (CS), business and financial data in the external data server (OS), and the like, arranges time information and the like, the formats of the acquired data are converted into formats appropriate for the correlation analysis (ASCA), and the data whose formats are converted are stored in the external data table (ASDT).

The external instrument control (ASMC) is a mechanism for controlling the external instrument (CM) connected to the application server (AS), and the external instrument control (ASMC) issues a control command in accordance with a control algorithm stored in the control target value (ASCT) so that the external instrument (CM) becomes in an appropriate state. It is conceivable that, as needed, the external instrument control (ASMC) sequentially acquires information of an external sensor (CS) that senses a subject on which the external instrument (CM) exerts an influence, and controls a drive device (CMAA) so that the sensed value becomes maximum (in other words, so that an after-mentioned brain index H becomes maximum). For example, if the external instrument is an air conditioner, a room thermometer is installed as the external sensor (CS), a room temperature that makes the brain index of a stayer in the room optimal is specified using the correlation analysis (ASCA), and a control command with the room temperature as a control target value is sent to the air conditioner. Similarly, it is possible to control the control method of environbrain BGM (control method of sound volume or selection method of a kind of music), the allocation method of passengers in an elevator or in an automobile, or the information service method about motor driving so that the brain index of a human is optimal.

Figure 5:
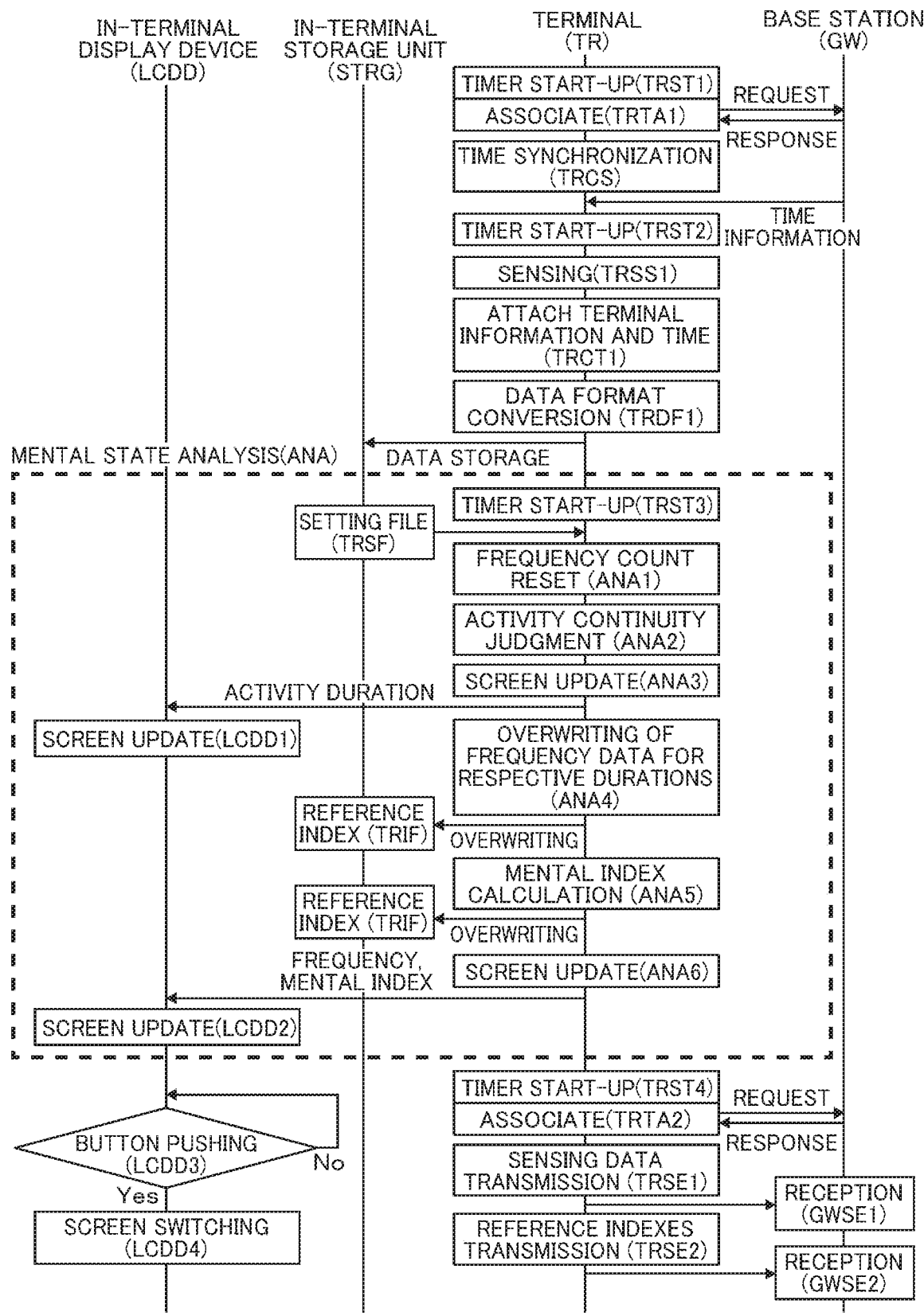
FIG. 5 is an example of a sequence diagram used for calculating brain indexes at the terminal.

<FIG. 5: Sequence of Brain Index Calculation at Terminal>

FIG. 5 is a sequence diagram showing the procedure of brain index calculation executed mainly at a terminal (TR) of this embodiment according to the present invention.

First, when the power supply of the terminal (TR) is turned on, and the associate relation is not established between the terminal (TR) and a base station (GW), the terminal (TR) regularly executes timer start-up (TRST1) to establish the associate relation. The associate relation between a terminal (TR) and a base station (GW) means a relation in which the terminal (TR) communicates with the base station (GW). After the terminal (TR) receives an associate response from the base station (GW) and the associate relation is established, the terminal (TR) executes time synchronization (TRCS). In the time synchronization (TRCS), the terminal (TR) receives time information from the base station (GW), and sets the clock (TRCK) of its own. The base station (GW) regularly communicates with the NTP server (TS) and corrects the time of its own. Therefore, times in all the terminals (TR) are synchronized. With this, in an after-executed analysis, it also becomes possible to compare and analyze sensing data among plural persons acquired at the same time by verifying time information attached to the data.

Timer start-up (TRST2) is executed on various sensors such as the three-axis acceleration sensor (AC) and temperature sensor (AE) of the terminal (TR) in constant periods, for example, in ten-second periods, and acceleration, sound, temperature, illuminance, and the like are sensed (TRSS1). The terminal (TR) detects that it is in a face-to-face situation with another terminal (TR) by transmitting its own terminal ID included in its terminal information (TRMT) and receiving the terminal ID of the another terminal (TR) via infrared communication. It is conceivable that the various sensors of the terminal (TR) always execute sensing without the timer start-up (TRST) being executed. However, executing the timer start-up in constant periods makes it possible to efficiently utilize the power supply of the terminal (TR), hence the terminal (TR) can be continuously used for a long time without the power supply being charged up.

The terminal (TR) attaches the time information of the clock (TRCK) and the terminal information (TRMT) to the sensed data (TRCT1). In the analysis of the data executed by the sensor net server (SS) or the application server (AS) afterward, persons that wear terminals (TR) can be identified using terminal information (TRMT) attached to the terminals (TR).

In data format conversion (TRDF1), the terminal (TR) attaches tag information regarding a sensing condition and the like to the sensing data, converts the format of the sensing data into a predefined transmission format, and stores the sensing data in the storage unit (STRG) in the terminal. This predefined transmission format is held in common in the data format information (GWMF) in the base station (GW) and in the data format information (SSMF) in the sensor net server (SS). Subsequently the converted sensing data is transmitted to the base station (GW).

The brain state analysis (ANA) regularly executes timer start-up (TRST3), and judges whether a person wearing the terminal is in an active state (or in a non-active state) from acceleration data in accordance with the read setting file (TRSF), and counts the active state duration. For example, if a frequency count and a brain index are calculated in one-day periods, the frequency count of the previous day is held in the storage unit (STRG) in association with the date of the previous day at a boundary time between days, which is predefined in the setting file (TRSF) (for example, at 2 o'clock in the morning), and a memory for frequency count is reset (ANA1) Afterward, for every predefined time unit (for example, every one minute), acceleration data is read, acceleration rhythm is calculated, and whether the person is in an active state or not is judged. If it is judged that the person has been in an active state continuously from the previous time unit (ANA2), the count of the duration is incremented, and the value of the active state duration displayed on the display device (LCDD) is updated ((ANA3) and (LCDD1)). In addition, in the reference index (TRIF), the frequency data in a range within which the above duration falls is overwritten (ANA4). Furthermore, the brain index is calculated again (ANA5) using a predefined function, and the value of the brain index is also overwritten. This function is an estimation expression whose arguments are the frequencies of specific active state durations as shown in FIG. 18(D). The updated frequency data and brain index are displayed on the display device (LCDD) ((ANA6) and (LCDD2)).

As for the screen display in the terminal (TR), it is conceivable that the display screen is switched (LCDD4) by pushing (LCDD3) any of the buttons (BTN).

In addition, after timer start-up (TRST4) is executed at a predefined time, and an association relation with a base station (GW) is established (TRTA2), the terminal (TR) transmits the difference between the current sensing data and the sensing data of the previous transmission and the difference between the current reference indexes and the previous reference indexes respectively to the base station (GW) ((TRSE1) and (TRSE2)). The base station receives both differences respectively ((GWSE1) and (GWSE2)).

Figure 6:
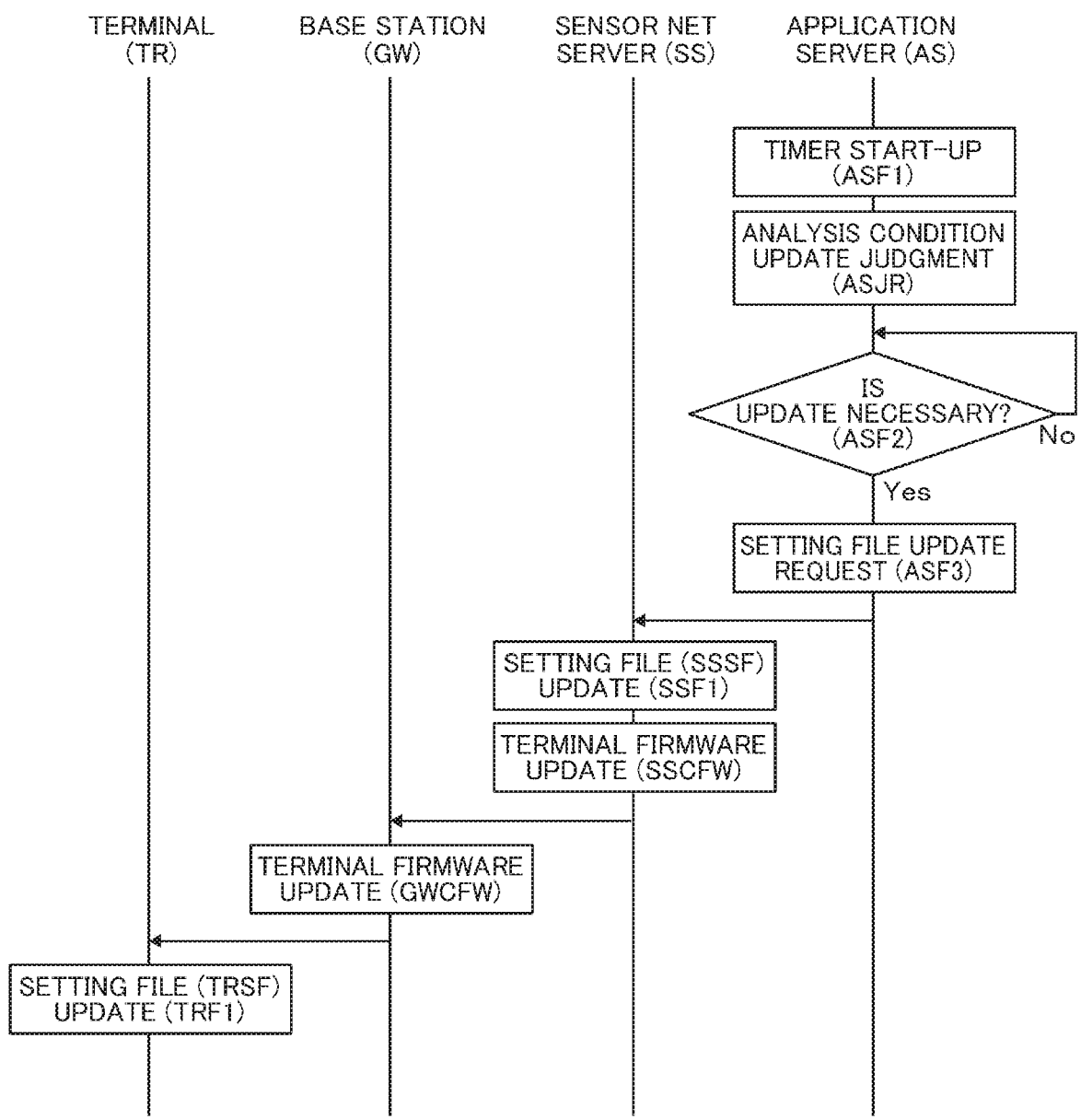
FIG. 6 is an example of a sequence diagram of processing for performing synchronization between setting files.

<FIG. 6: Sequence of Setting File Synchronization>

Because it is desirable that a value that is checked by a user (US), who is wearing a terminal (TR), using a display device (LCDD) and a value that is checked afterward on the screen (OD) of a client (CL), it is necessary that a brain index acquired as a result of the brain state analysis (SS-CDT) at the sensor net server (SS) should coincide with a brain index acquired as a result of the brain state analysis (ANA) at the terminal (TR). Therefore, it is necessary that the setting values of a function for calculating the brain index in the setting file (SSSF) in the sensor net server (SS) and those in the setting file (TRSF) in the terminal (TR) should be in synchronization with each other. FIG. 9 shows examples of setting values that should be in synchronization with each other in the two setting files (SSSF) and (TRSF). Those values include, for example, range definition (LD) used for sorting the durations of an active state, the threshold of an acceleration frequency (SF_TH) used for the judgment of an active state, a time (SF_RE) at which the date is updated when a brain index is calculated in one-day periods, an expression (SF_EQ) for calculating a brain index.

FIG. 6 shows a sequence diagram of processing for performing synchronization between the setting file (SSSF) in the sensor net server (SS) and the setting file (TRSF) in the terminal (TR).

In the application server (AS), after timer start-up (ASF1) is executed, the analysis condition update judgment (ASJR) is executed, and in the case where the change of an analysis condition is transmitted from the client (CL) or in the case where it is judged that a more appropriate value can be obtained if the setting values in the setting file (SSSF) and in the setting file (TRSF) are changed as a result of the correlation analysis (ASCD) which is executed using a brain index acquired from regular questionnaires (ASF2), setting file update request (ASF3) is transmitted. After the sensor net server (SS) receives the above request, the sensor net server (SS) updates (SSF1) the relevant part of the setting file (SSSF) of its own, and further activates the terminal firmware update (SSCFW) to transmit an update command for updating the setting file in a terminal (TR) to the base station (GW). The base station (GW) activates the terminal firmware update (GWCFW), and transmits the above update command to all the terminals (TR) ruled by itself or to specified terminals (TR). Each terminal (TR) that receives the command overwrites the relevant part of the setting file (TRSF) (TRF1).

Figure 7:
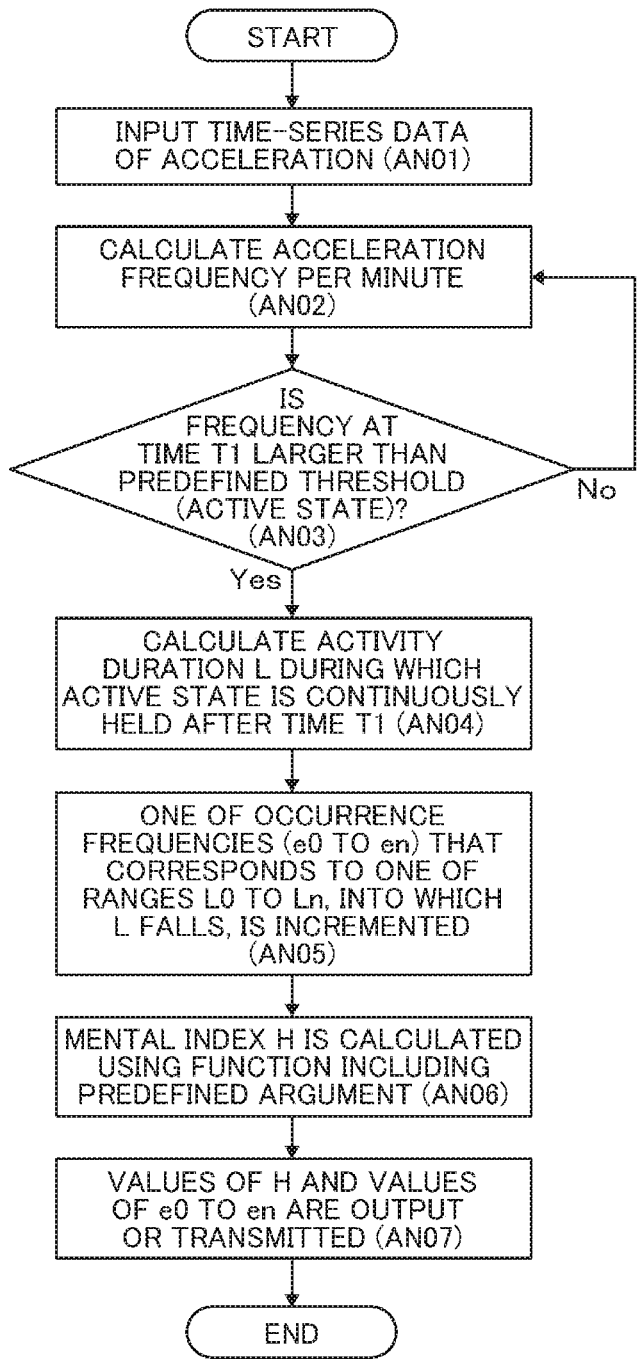
FIG. 7 is an example of the flowchart of brain state analysis processing.

<FIG. 7: Flowchart of Brain State Analysis>

FIG. 7 shows the flowchart of a brain state analysis. Furthermore, FIG. 8 shows a table for explaining the calculation procedure of the brain state analysis using an example.

This flowchart is a flowchart commonly used in the brain state analysis (ANA) in the terminal (TR) and in the brain state analysis (SSDT) in the sensor net server (SS), and if reference indexes calculated in the terminal (TR) are stored in the index storage table (SSDT), and the reference indexes are used for the display screen generation (ASCD) and the correlation analysis (ASCA), the brain state analysis (SSCDT) in the sensor net server (SS) can be omitted. Alternatively, using the value of an occurrence frequency output in specified periods (for example, in one-day periods) by the brain state analysis (ANA) in the terminal (TR), only step (AN06) and later can also be calculated again in the brain state analysis (SSCDT) in the sensor net server (SS) as brain indexes during plural periods or brain indexes of a group including plural persons.

As for the procedure of the analysis, the time-series data of acceleration is input (at step AN01) first, and an acceleration frequency is calculated in predefined periods (for example, in one-minute periods) (AN02). In this case, if the sensor is a three-axis acceleration sensor, the geometric average of three-axis acceleration values is calculated every sensing time period $\Delta t$ (for example, every 0.01 seconds) to obtain one positive value, and a frequency is calculated using the time-series data F(t) of plural positive values obtained in the above way. As a method for calculating the frequency, an existing method such as Fast Fourier transformation can also be used. As one of methods for reducing a calculation amount in the terminal (TR), there is a method in which the time-series data F(t) is roughly processed in n×$\Delta t$ periods, new time-series data G(t) is created using the differences between the values at the time t and the values at the time t+$\Delta t$, and the number of times the time-series data G(t) crosses zero can be counted instead of counting the number of peaks of the time-series data F(t) for convenience. Examples in the column (t0804) show integer numbers obtained by multiplying the values of frequencies by 100.

Next, whether an acceleration frequency is equal to or larger than a predefined threshold or not is judged in unit time periods (for example, in one-minute periods), and if the acceleration frequency is equal to or larger than the predefined threshold, it is judged that a person wearing the terminal (TR) is in an active state (AN03) (t0805). If the person is in an active state at the time Ti, the length of a time period during which the person is continuously in an active state afterward is counted (t0806), and an active state duration L is calculated (AN04) (t0807). Next, a range (any of L0 to Ln) within which the active state duration L falls is determined in accordance with the range definition (LD) specified in the setting file (SSSF) or in the setting file (TRSF), and a count of an occurrence frequency (any of e0 to en) corresponding to the determined range is incremented (AN05).

Subsequently, a happiness index per day is calculated using the expression (SF_EQ) including arguments (for example, e1 and e3) specified by the setting file (SSSF) or the setting file (TRSF). Lastly, the brain index H and, if needed, the values of the occurrence frequencies (some of e0 to en) are output or transmitted to the next step as the reference indexes (AN07). In the case where this analysis is executed in the terminal (TR), the above values are stored in the reference index (TRIF), and then transmitted to the base station (GW), and in the case where this analysis is executed in the sensor net server (SS), the above values are stored in the index storage table (SSDT).

<FIG. 18: Knowledge about Brain Index Calculation>

FIG. 18(A) to (D) are diagrams for explaining the knowledge of the inventors who have confirmed that the feeling of happiness or feeling of dysphoria of a person exerts an influence on the duration of his/her physical exercise.

FIG. 18(A) is a diagram for explaining an active state duration L, and the vertical axis represents the activity state of the person, which is judged by whether an acceleration frequency is equal to or larger than a threshold or not, by a binary.

FIG. 18(B) is a diagram showing the distributions of active state durations acquired from the frequencies of acceleration data obtained by actual wearable sensors, and the active state durations are shown after being classified into data about low-stressed persons and data about high-stressed persons on the basis of questionnaire executed about stress. Judging from this result, we have confirmed that the distribution of active state durations provided by a human being has a certain tendency and that the gradient of the distribution vary in accordance with the level of the relevant stress. In addition, in order to research ranges L1 and L2, within each of which a large difference between the two above kinds of active state durations occurs, the brain indexes of plural persons are collected using a questionnaire method such as CES-D method, and it has been confirmed that the value HO of brain index can be sufficiently estimated using the linear sum of frequencies of active state duration within two kinds of ranges (FIG. 18(C)). FIG. 18(C) is the distribution comprised of the average values per group obtained by a questionnaire and estimated values H obtained using a calculation expression shown in FIG. 18(D). Judging from FIG. 18(C), it can be confirmed that the average values per group obtained by the questionnaire are sufficiently estimated in terms of accuracy by the calculation expression.

FIG. 18(D) shows the calculation expression for estimating a brain index (a value showing the feeling of happiness, that is, a happiness level). The brain index H is represented by the linear sum of frequencies of active state duration within at least two kinds of ranges. Constants a, b1, and b2 are decided so that the brain index H given by the calculation expression maximally approximates a value obtained by the questionnaire. Furthermore, as one of the features, the calculation expression includes the coefficient of one term including one frequency is a negative value, and the coefficient of the other term including the other frequency is a positive value. This can be understood as follows: there is a trade-off between the coefficient allocated to one term and the coefficient allocated to the other term because there is the upper limit of active time in a day. In addition, a conclusion that a range L1 included in the term having the negative coefficient is smaller than a range L2 included in the term having the positive coefficient has already been obtained, and it has been revealed that, in the case where the durations of an active state are short but the active state occurs many times, the stress is light. Here, a measurement time T is equivalent to the number of measured data in a day. By dividing a frequency e by T, the occurrence probability of a duration that falls in a range corresponding to e is obtained, and a brain index is given by a linear sum of some occurrence probabilities.

To sum up the above, the brain state analysis system, which analyzes the brain state of a person, according to this embodiment, includes a terminal (TR) is worn on the body of a person. The terminal (TR) includes: an acceleration sensor (AC) for measuring the acceleration of motion of the body; a storage unit (STRG) for storing time-series data (SENSD) and a threshold (SF_TH) of the acceleration; and a processing unit (ANA) for performing processing (AN03) for determining whether each value (t0804) contained in the time series data (SENSD) is in a first state (active state) in which the value is equal to or greater than the threshold or in a second state (non-active state) in which the value is less than the threshold, processing (AN04) for determining a duration (L) which is a period of time during which the first state continues, and processing (AN06) for quantifying the brain state of the person on the basis of the duration (L). Thanks to the above characteristic configuration, the brain state analysis system according to this embodiment can provide the duration of an active state desirable for a worker, so that the worker can amend his/her conduct code bearing his/her conduct in mind so that the duration of the desirable active state is increased. On the other hand, in the case where the duration of an undesirable active state is provided, the worker can amend his/her conduct code by making efforts to reduce the duration of the undesirable active state.

To put it more concretely, it is recommendable that the processing unit (ANA) quantifies the brain state on the basis of the occurrence frequencies (e1/T and e2/T) of the duration included in plural regions (L1 and L2) each of which has a predefined range within which the duration falls. With this, because a range of duration desirable and a range of duration undesirable for the brain state of a worker can be provided, it becomes easy for a wearer of the terminal (TR) to amend his/her conduct code. In this case, the above plural regions includes a first region (L1) having a first range within which the duration falls and a second region (L2) having a second range within which the duration falls, and it is preferable that the upper limit of the second range should be larger than the upper limit of the first range. This is because the above setting can clarify the ranges that have the abovementioned trade-off relation with each other.

To put it more concretely, it is preferable that the processing unit (ANA) should quantifies the brain state using the sum of a first term that includes a first occurrence frequency (e1/T) that is the occurrence frequency of the duration included within the first region and a second term that includes a second occurrence frequency (e2/T) that is the occurrence frequency of the duration included within the second region. Furthermore, it is recommendable that, of a term regarding the first occurrence frequency and a term regarding the second occurrence frequency, one has a negative coefficient and the other has a positive coefficient, and the sum of both terms is calculated. The above is derived from the knowledge explained using FIG. 18, and thanks to the above configuration of the estimation expression, it becomes possible to calculate a distribution that well approximates an average value obtained from a questionnaire, hence the brain state of a person can be retrieved more accurately.

In addition, the brain state measurement system further includes an external sensor (CS) that measures sensor information regarding circumstances in which a person resides, an external instrument (CM) that has a function to change sensor information, and an application server (AS). In this case, it is preferable that the application server (AS) executes processing (ASCA) for analyzing the correlation between the brain state quantified by the processing unit (ANA) and the sensor information, and further executes processing (ASMC) for making the external instrument execute control for changing the sensor information on the basis of the result of the correlation analysis so that the value of the brain state is increased. Because the application server (AS) is configured in such a way, it becomes possible to control the external instrument so that the brain index of a person becomes optimal.

From another viewpoint, the brain state measurement system according to this embodiment, which analyzes a brain state of a person, includes a terminal (TR) to be worn on the person's body. The terminal (TR) includes an acceleration sensor (AC) for measuring the acceleration of motion of the body, and an processing unit (ANA) for calculating a first brain index that shows the brain state of the person in a first time period and a second brain index that shows the brain state of the person in a second time period on the basis of the time-series data of the acceleration (SENSD). The processing unit (ANA) can be considered to be a unit that quantifies an influence that is exerted on the brain state of a person by sensor information regarding the behavior of the person or regarding circumstances in which the person resides on the basis of the first and second indexes (H) and a first value of the sensor information in the first time period and a second value of the sensor information in the second time period, wherein the information regarding the behavior of the person is, for example, information about the number of steps obtained from a three-axis acceleration sensor (AC), and the sensor information regarding circumstances in which the person resides is, for example, various types of information obtained from external sensors (CS), face-to-face information obtained from an infrared transmission/reception unit (AB), sound information obtained from a microphone (AD), temperature information obtained from a temperature sensor (AE). In this case, it is assumed that the calculation method of a brain index (H) is the method explained using FIG. 18, but this is not only one method, and other methods can also be used. With the use of the above-described way, it becomes possible to quantify an influence exerted on the brain state of a person by a change of sensor information, hence the sensor information can be controlled so as to provide an optimal value to the person using a value obtained by quantifying the influence.

Figure 10:
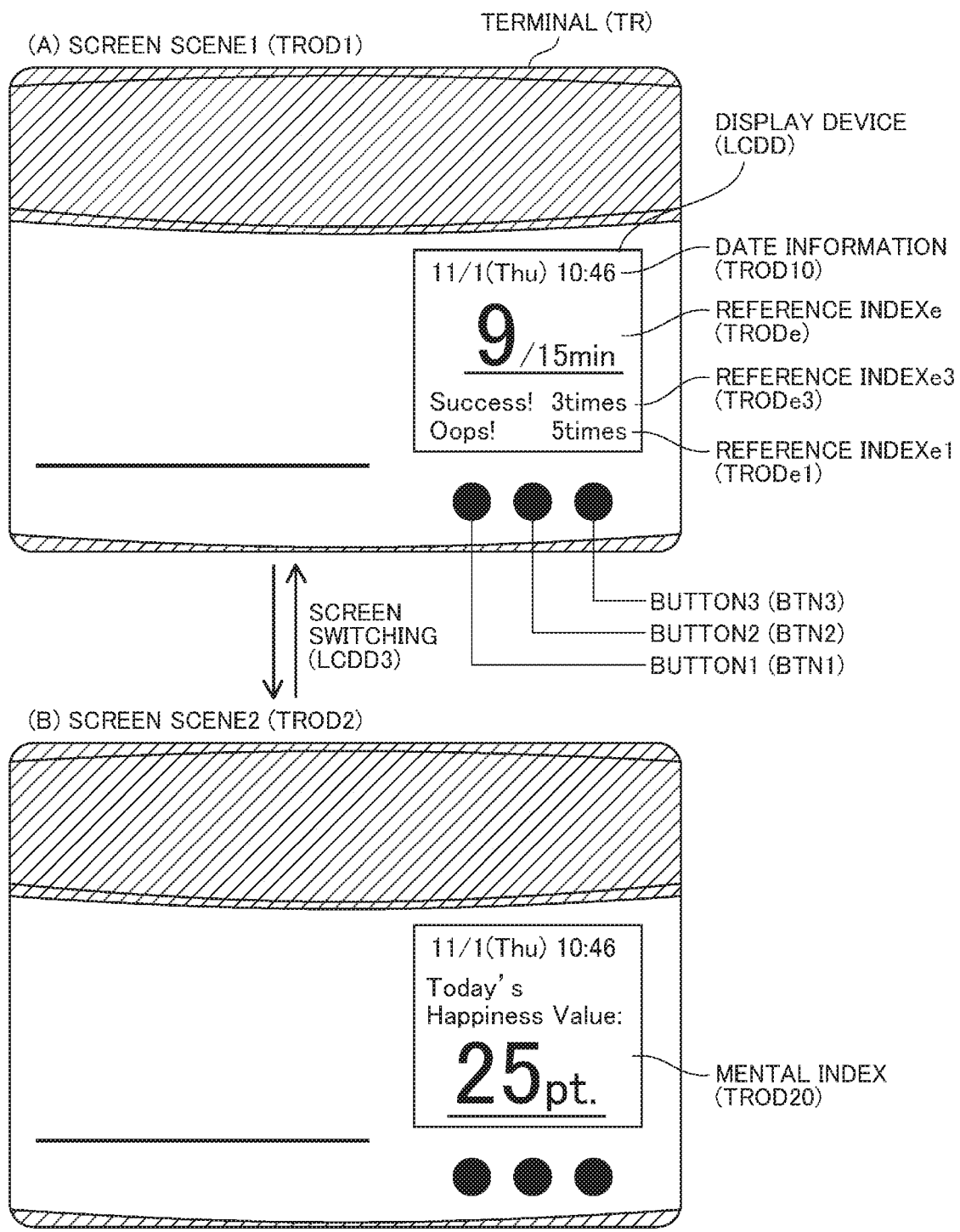
FIG. 10 is an example of a diagram for explaining the display screen of the terminal.

<FIG. 10: Example of Display Screen of Terminal>

FIG. 10 shows an example of a display screen (LCDD) of a terminal (TR) that is used for measuring a brain state and is discovered on the basis of the knowledge explained with reference to FIG. 18. This terminal calculates a brain index (TROD20) using acceleration frequencies obtained from a predefined time (for example, 2 o'clock in the morning) to the current time, and displays the brain index (TROD20). The display content of the screen can be switched by pushing some buttons (BTN1 to BTN3) (LCDD3). If it is not preferable that a brain index (TROD20) meets others' eyes when a person is wearing a terminal (TR), the display screen can be configured in such a way that another screen 1

(TROD1) is usually displayed, and the brain state (TROD20) is displayed during a predefined time period after a button is pushed (TROD2).

For example, it is also possible to display an active state duration in normal times. With this, motivation to continue the active state can be given to the person. For example, in the case of the setting files (SSSF) and (TRSF) shown in FIG. 9, it can be understood that, if a duration is equal to 5 minutes or larger and smaller than 10 minutes, the duration gives a negative influence (an undesirable influence) to the brain state of the person, and if the duration is equal to 15 minutes or larger and smaller than 20 minutes, the duration gives a positive influence (a desirable influence) to the brain state of the person. The numbers of occurrence frequencies in these ranges in a day are displayed with explanatory notations "Oops!" (TRODe1) and "Success!" (TRODe3) respectively. Furthermore, it is also conceivable that, if it is set as a target to continue being in an active state for 15 minutes, the duration of the active state from the time point when the previous active state stopped to the current time is additionally displayed (TRODe).

As described above, the display unit (LCDD) according to this embodiment displays the duration (TRODe), and the occurrence frequencies (TRODe1) and (TRODe3) of the duration included in a certain region which has a predefined range within which the duration falls, or the value of the quantified brain state (TROD20). The above-described display way makes it possible to give motivation to a worker more appropriately. Especially, it is recommendable that the first occurrence frequency that is the occurrence frequency (TRODe1) of the duration falling in the first region (L1) and the second occurrence frequency that is the occurrence frequency (TRODe3) of the duration falling in the second region (L2) are displayed. In addition, it is desirable that the upper limit of the second range should be larger than the upper limit of the first range. Because of the above-described display way, it becomes easy for a worker to grasp a desirable conduct and an undesirable conduct that are specified on the basis of the knowledge explained with reference to FIG. 18, which makes it possible to give motivation to the worker more accurately.

Figure 11:
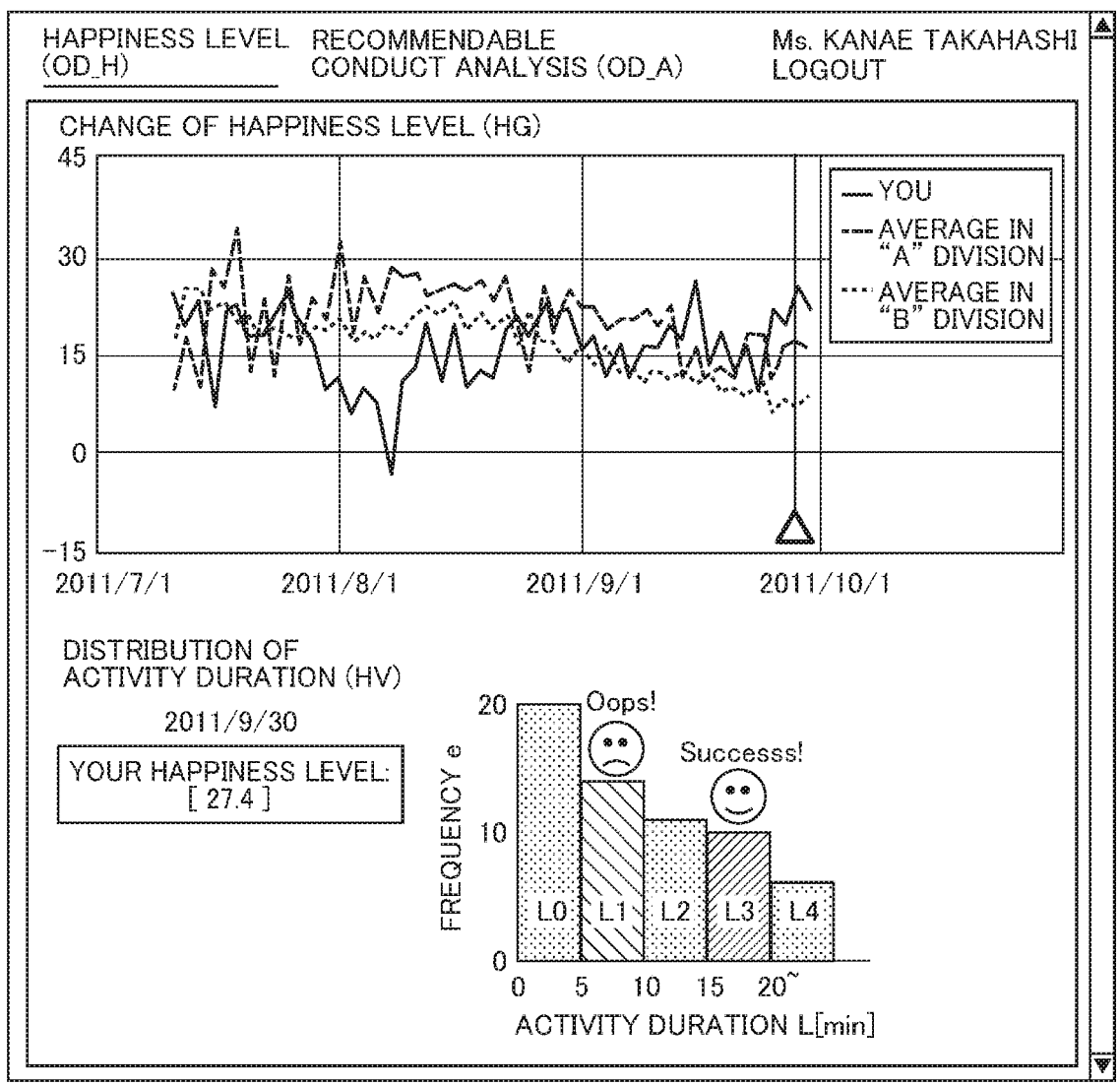
FIG. 11 is an example of a diagram showing the screen of a Web application showing a brain index.
Figure 12:
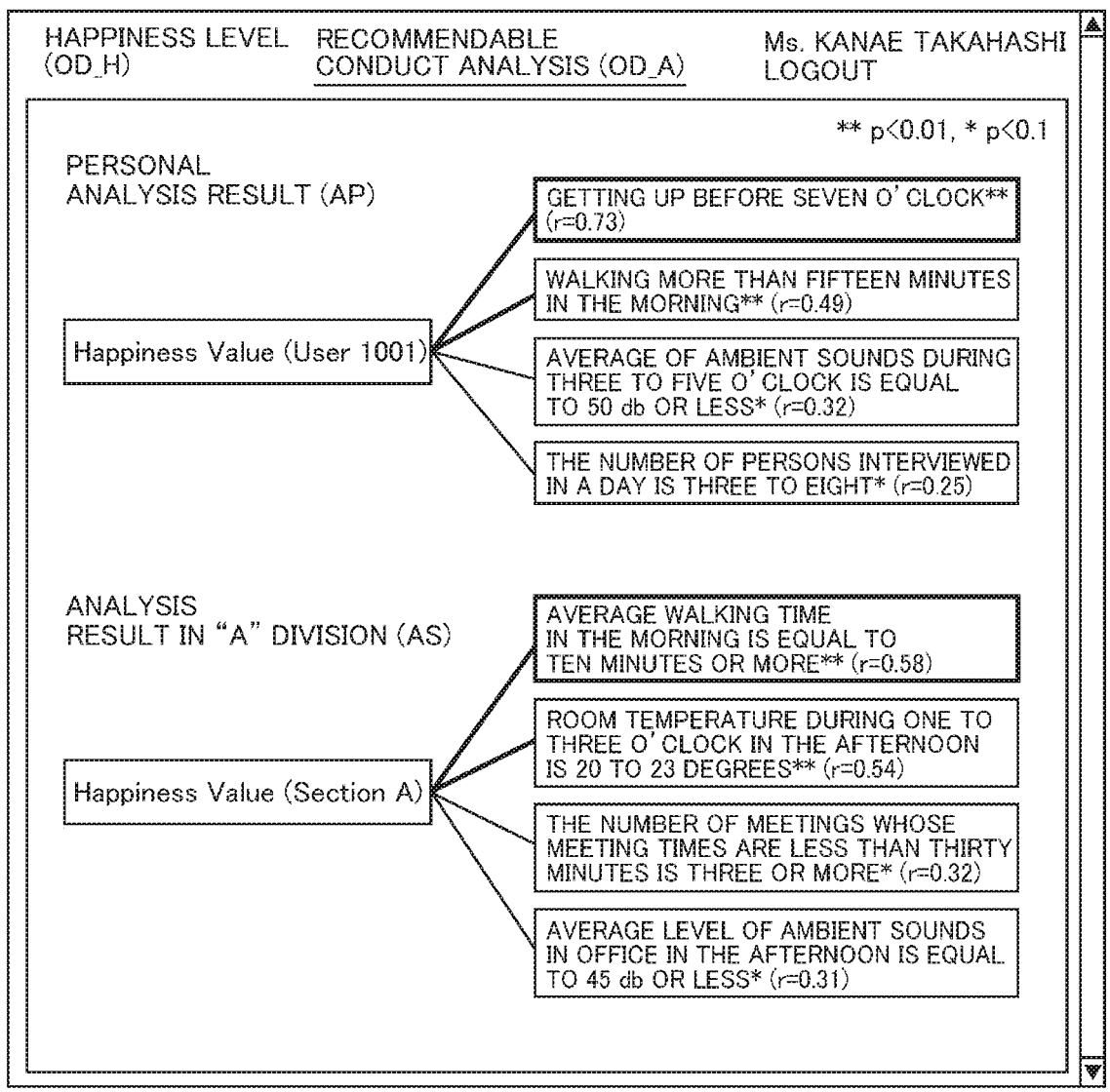
FIG. 12 is an example of a diagram showing the screen of a Web application showing a correlation analysis result between a brain index and other indexes.

<FIG. 11, FIG. 12, and FIG. 13: Examples of Display Screens of Web Application>

FIG. 11 and FIG. 12 are examples of display screens (OD) generated by the display screen generation (ASCD).

FIG. 12 shows an example of a screen for a user (US) to check the brain index of his/her own or the brain index of a section to which the user (US) belongs. For example, a graph (HG) shows the variations of the time-series of the brain indexes of the user (US), the section to which the user (US) belongs, and the like. Furthermore, it is also conceivable that the distribution of the active state duration (HV), which is an argument of the brain index, is displayed in a graph so that the occurrence frequencies within a desirable range and the occurrence frequencies within an undesirable range can be checked. With this, what differences there are between a day with the high brain index and a day with the low brain index can be checked, and the user (US) himself/herself can examine measures for heightening the brain state in association with events that occur in a day.

In addition, FIG. 12 is a screen (OD) showing an example of the result of a correlation analysis (ASCA). After a calculated brain index is set as a target variable, and indexes regarding circumstances and instrument operations and conduct indexes are set as explanatory variables, a statistical analysis is executed, and strongly-correlated explanatory variables are extracted, and displayed. In this case, it is also conceivable that the analysis result regarding a person (AP) and the analysis result regarding a section (AS) are written separately.

FIG. 13 shows an example of an index storage table (SSDT) regarding one user (US). The screens shown in FIG. 10, FIG. 11, and FIG. 12 are generated after the values stored in the index storage table (SSDT) are read. Although the reference index (TRIF) in a terminal (TR) also has the same items, if the storage capacity of the reference index (TRIF) is small, the reference index (TRIF) can be specified so as to store data for only several days. The index storage table (SSDT) stores frequencies (e0 to e4) sorted for respective specified ranges L, total measurement times T, and the estimation values (H) of brain indexes. Additionally, although it is conceivable that the index storage table (SSDT) stores data of the results of conduct distinguishment (SSCAD) and the like, a column to store this data is omitted in FIG. 13.

<FIG. 14: Example of User Attribute List>

FIG. 14 is an example of the format of a user attribute list (ASUL) stored in the storage unit (ASME) of the application server (AS). The user attribute list (ASUL) records User Number (ASUIT1), User Name (ASUIT2), Terminal ID (ASUIT3), Department (ASUIT4) and Section (ASUIT5) to which users belong in association with each other. User Number (ASUIT1) shows serial numbers corresponding to existing users. Furthermore, User Name (ASUIT2) shows the names or nicknames of the users (US) used when display screens and contents are generated, and Terminal ID (ASUIT3) shows pieces of terminal information possessed by the users (US). User (US) and Terminal ID (ASUIT3) correspond to each other one-on-one. In addition, Department (ASUIT4) and Section (ASUIT5) are information about organizations to which users (US) belong, and for example, if fundabrain contents are generated in units of organizations, members to be included in data are specified on the basis of this information.

In addition, although pieces of information about users and organizations to which the users belong are provided in a tabular format in FIG. 14, these pieces of information can be provided hierarchically using XML or the like. In this case, the organization of a company can be expressed according to the organizational hierarchy of the company in such a way that there is A department under A company, A1 section under A department, and so on, and the user name and terminal ID of a person can be expressed under the relevant organization. Here, because there may be a case where the same person belongs to plural organizations in reality, it sometimes happens that there is a user under plural organizations.

<FIG. 15: Example of Sensing Database (SSDB): Acceleration Table>

FIG. 15 shows data stored in an acceleration data table (SSDB_ACC_1002) as examples of sensing data stored in the sensing database (SSDB) in the sensor net server (SS). The data is fundabrainly raw sensing data acquired at a terminal (TR) and it is not preprocessed. One acceleration data table is generated for one person, and acceleration data in the X-axis direction (DBAX), acceleration data in the Y-axis direction (DBAY), and acceleration data in the Z-axis direction (DBAZ) are acquired and stored in certain sampling periods (for example, in 0.02-second periods) in association with time information (DBTM). Here, raw numerical values detected by an acceleration sensor can be stored as they are, or numerical vales obtained by converting the unit of data into gravitational unit [G] can be stored. Such an acceleration data table is generated for each member, and each of sensed data is stored in association with time information regarding the time when each of the data is sensed. Here, if a column showing user IDs is added to an acceleration data table, plural acceleration data tables can be integrated into one table without generating one acceleration data table for one person.

<FIG. 16: Example of Sensing Database (SSDB): Face-to-Face Table>

Although a sensing database (SSDB) records plural kinds of sensing data of plural members, examples of tables collecting face-to-face data obtained through infrared transmission/reception are shown in FIGS. 16(A) and (B). FIG. 16(A) shows a face-to-face table (SSDB_IR_1002), and it is assumed that the face-to-face table (SSDB_IR_1002) collects data obtained by a terminal (TR) with its terminal ID 1002. Similarly, FIG. 16(B) shows a face-to-face table (SSDB_IR_1003), and it is assumed that the face-to-face table (SSDB_IR_1003) collects data obtained by a terminal (TR) with its terminal ID 1003. Here, if a column showing infrared reception side IDs is added to the face-to-face table, it is not necessary to provide one face-to-face table for one terminal (TR) that is used for obtaining data. Furthermore, it is conceivable that other data regarding acceleration and temperature is included in the same table.

The face-to-face tables shown in FIGS. 16(A) and (B) are examples that store times (DBTM) at which terminals (TR) transmit data, infrared transmission side IDs (DBR1), and the number of times (DBN1) the terminals (TR) receives data from the infrared transmission sides having the IDs, where the infrared transmission side IDs and the number of times are stored in the form of couples (a couple of DBR1 and DBN1 to a couple of DBR10 and DBN10). If each of the terminals transmits data once every ten seconds, each of these tables shows how many times each of the terminals receives data through infrared communication during ten seconds after each of the terminals transmits data last time. It means that even in the case where each of the terminals meets plural terminals (TR) face-to-face, each of the face-to-face tables is configured to store up to ten couples. Here, the maximum number of couples can be freely set. If there is no face-to-face contact, in other words, if there is no infrared reception, the value written in the relevant field in the table is expressed by null. In addition, although time is expressed to the millisecond in each of the tables shown in FIGS. 16(A) and (B), the expression format of time can be any format as long as the format is clearly defined.

<FIG. 17: Example of Sensing Database (SSBB): Conduct Rhythm Table>

The result of acceleration frequency calculation (AN02) in brain state analysis (ANA) and (SSCDT) can be output to the sensing database (SSDB) as time-series data. An example of an acceleration frequency table (SSDB_ACCTP_1 min) is shown in FIG. 17. The acceleration frequency table (SSDB_ACCTP_1 min) stores a frequency regarding each user (US) calculated in constant periods (for example, in one-minute periods) on the basis of the acceleration data table (SSDB_ACC) in association with the relevant calculation time and the user ID of each user (US). Here, a format that is used for storing the above data can be a format other than a tabular format, for example a CSV file format.

Although an embodiment of the present invention has been described so far, it should be understood by those skilled in the art that the present is not limited to the above embodiment, and that various changes may be made and appropriate combinations of the above-described embodiments may also be made.

REFERENCE SIGNS LIST

TR, TR2, TR3: Terminals
GW: Base Station
US, US2, US3: Users
NW: Network
PAN: Personal Area Network
SS: Sensor Net Server
AS: Application Server
CL: Client
OS: External Data Server
CM: External Instrument
CS: External Sensor.

The invention claimed is:

1. An analysis system that analyzes a state of a person, the analysis system comprising:
    a terminal configured to be worn on the person's body, the terminal including:
        an acceleration sensor that measures an acceleration of motion of the person's body;
        a storage unit that stores time-series data and a threshold of the acceleration; and
        a processing unit that: i) determines whether each value contained in the time series data is in a first state in which the value is equal to or greater than the threshold or in a second state in which the value is less than the threshold, ii) determines a duration which is a period of time during which the first state continues, iii) quantifies a brain state of the person based on the duration, and iv) calculates a brain index based on the brain state, wherein
    the processing unit quantifies the brain state based on occurrence frequencies of the duration included in a plurality of regions each of which has a predefined range within which the duration falls,
    the plurality of regions includes a first region having a first range within which the duration falls and a second region having a second range within which the duration falls,
    an upper limit of the second range is larger than an upper limit of the first range,
    the brain state is quantified by calculating a sum of a first term that includes a first occurrence frequency that is an occurrence frequency of the duration included within the first region and a second term that includes a second occurrence frequency that is the occurrence frequency of the duration included within the second region,
    the calculated brain index is calculated by the processing unit using coefficients.

2. The analysis system according to claim 1, wherein the brain state is quantified by calculating the sum of the first and second terms, one of which has a negative coefficient and the other of which has a positive coefficient.

3. The analysis system according to claim 1,
    wherein the terminal includes a display unit that displays the duration, and the occurrence frequencies of the duration included in a certain region which has a predefined range within which the duration falls, or a value of the quantified brain state.

4. The analysis system according to claim 3, wherein the display unit displays the first occurrence frequency and the second occurrence frequency.

5. The analysis system according to claim 1, further comprising:
    an external sensor that measures information regarding circumstances in which the person resides;

an external instrument that changes the sensor information; and an application server, wherein the application server executes correlation analysis between the quantified brain state and the sensor information, and causes the external instrument to change the sensor information based on a result of the correlation analysis so that a value of the brain state is increased.

* * * * *